(12) United States Patent  (10) Patent No.: US 8,183,385 B2
DeMattei et al.  (45) Date of Patent: May 22, 2012

(54) SNAR PROCESS FOR PREPARING BENZIMIDAZOLE COMPOUNDS

(75) Inventors: John DeMattei, San Diego, CA (US); Sagar Shakya, Longmont, CO (US); Paul J. Nichols, Boulder, CO (US); Bradley R. Barnett, Boulder, CO (US); Bruno P. Hache, Boulder, CO (US); Matthew Charles Evans, Macclesfield (GB); James Gair Ford, Macclesfield (GB); John Leonard, Macclesfield (GB)

(73) Assignees: Array BioPharma Inc., Boulder, CO (US); AstraZeneca AB, Sodertalje (SE)

( * ) Notice: Subject to any disclaimer, the term of this patent is extended or adjusted under 35 U.S.C. 154(b) by 513 days.

(21) Appl. No.: 11/917,998

(22) PCT Filed: Jun. 21, 2006

(86) PCT No.: PCT/US2006/023986
§ 371 (c)(1),
(2), (4) Date: Jan. 26, 2010

(87) PCT Pub. No.: WO2007/002092
PCT Pub. Date: Jan. 4, 2007

(65) Prior Publication Data
US 2010/0130748 A1    May 27, 2010

Related U.S. Application Data

(60) Provisional application No. 60/693,374, filed on Jun. 23, 2005.

(51) Int. Cl.
C07C 235/08    (2006.01)
(52) U.S. Cl. .................................. 548/304.4
(58) Field of Classification Search ............... 548/304.4
See application file for complete search history.

(56) References Cited

U.S. PATENT DOCUMENTS 6,582,351 B1    6/2003    Sawada et al.
(Continued)

FOREIGN PATENT DOCUMENTS

WO    00/42022 A1    7/2000
(Continued)

OTHER PUBLICATIONS

Rogers, G. T. et al, A Novel Von Richter Reaction, Tetrahedron Letters, 1968, pp. 1029-1032, vol. 9, Pergamon Press, Great Britain.
(Continued)

*Primary Examiner* — Joseph Kosack
*Assistant Examiner* — Matthew Coughlin
(74) *Attorney, Agent, or Firm* — John R. Moore, Esq.; Sarah S. Mastous; Viksnins Harris & Padys PLLP

(57) ABSTRACT

Provided are methods for the synthesis of heterocyclic compounds such as benzimidazole carboxylic acid core structures having Formula Ia-2 and their synthetic intermediates: wherein $X^1$, $X^2$, $X^5$, $R^1$, $R^2$ and $R^4$ are as defined herein. Compounds of Formula Ia-2 and their synthetic intermediates can be used to prepare heterocyclic derivatives such as benzimidazole derivatives.

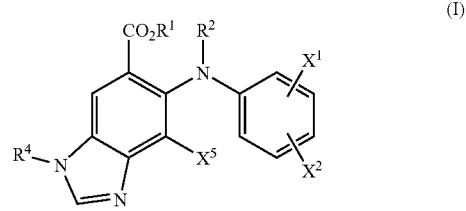

39 Claims, 7 Drawing Sheets

U.S. PATENT DOCUMENTS 7,160,915 B2 1/2007 Barrett et al.
2003/0232869 A1 12/2003 Wallace et al.

FOREIGN PATENT DOCUMENTS

WO 03077914 A1 3/2003
WO WO 03077914 A1 * 9/2003
WO 2005009975 A2 2/2005

OTHER PUBLICATIONS

Zefirov, N.S. et al., "Solid-Phase Synthesis of 1,2-Benzophenazine and Some Fused Imidazole Derivatives", Chemistry Department of the Moscow State University, Moscow, Russia, 4 pages.

Milata V. et al., "Simple and Convenient Procedure for the Preparation of 1-Methyl-4-Nitrobenzimidazole", Department of Organic Chemistry, Faculty of Chemical Technology, Slovak Technical University, vol. 25, No. 6, 1993.

Morgan, G.T. et al., "Bases derived from 2-Chloro-4:5-dinitrotoluene", CLXXX.—Ortho-Chlorodinitrotoluenes. Part III. pp. 1537-1546.

Ellis, G.P. et al., "One-Step Synthesis and Spectral Study of Some 1-Methylbenzimidazoles, including Use of a Lanthanide Shift Reagent", J.C.S. Perkin 1, 1974, pp. 903-906.

* cited by examiner

SNAR PROCESS FOR PREPARING BENZIMIDAZOLE COMPOUNDS

RELATED APPLICATION

The present invention claims priority of U.S. Provisional Application Ser. No. 60/693,374 filed Jun. 23, 2005, which is incorporated herein in its entirety by this reference.

BACKGROUND OF THE INVENTION

1. Field of the Invention

This invention relates to processes for the preparation of heterocyclic compounds. More specifically, this invention relates to the synthesis of compounds that can be used to prepare pharmaceutical agents such as benzimidazole derivatives. This invention further includes intermediate compounds obtained during the synthesis of the heterocyclic compounds of this invention and to the methods of preparation thereof.

2. Description of the State of the Art

Benzimidazole derivatives have been investigated as therapeutics for treating cancers, viral infections, and diseases and pathological conditions involving inflammation and have been disclosed in a number of patents and publications in the last several years, including U.S. Patent Publication Nos. 2003/0232869, 2004/0116710, and 2003/0216460; U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; WO 02/06213; WO 03/077914; and WO 03/077855.

In particular, WO 03/077914 describes the synthesis of the sodium salt of a benzimidazole derivative 11 from 2,3,4-trifluorobenzoic acid in 11 linear steps as illustrated in Scheme 1. Introduction of a di-substituted aniline is accomplished by the stepwise introduction of an unsubstituted aniline moiety, followed by subsequent bromination and chlorination. Not only is this process inefficient in terms of the number of linear synthetic steps required, but there are also selectivity issues, as well as process safety issues around the chlorination reaction. For example, the synthesis shown in Scheme 1 includes a number of chemical transformations that could be hazardous to carry out on a manufacturing scale, and/or produce levels of by-products that would not be acceptable in a final active pharmaceutical ingredient (API). It will be appreciated by those skilled in the art that for a process to be suitable for industrial application it should be (i) amenable to being performed on large scale, (ii) have minimal environmental impact (for example in terms of amount of raw materials required and/or the amount of waste produced), (iii) safe (for example, use materials of low toxicity that do not produce toxic waste), and (iv) as low in cost as possible (for example, by being a higher yielding and more convergent synthesis). Since heterocyclic compounds such as benzimidazoles are potentially useful as therapeutics, there is an on-going need for a more efficient synthetic route for the production of benzimidazole derivatives that is more suitable for large-scale manufacture. A single step procedure that would allow the introduction of substituted aniline would therefore be extremely useful for the purpose of manufacturing benzimidazole derivatives.

Scheme 1

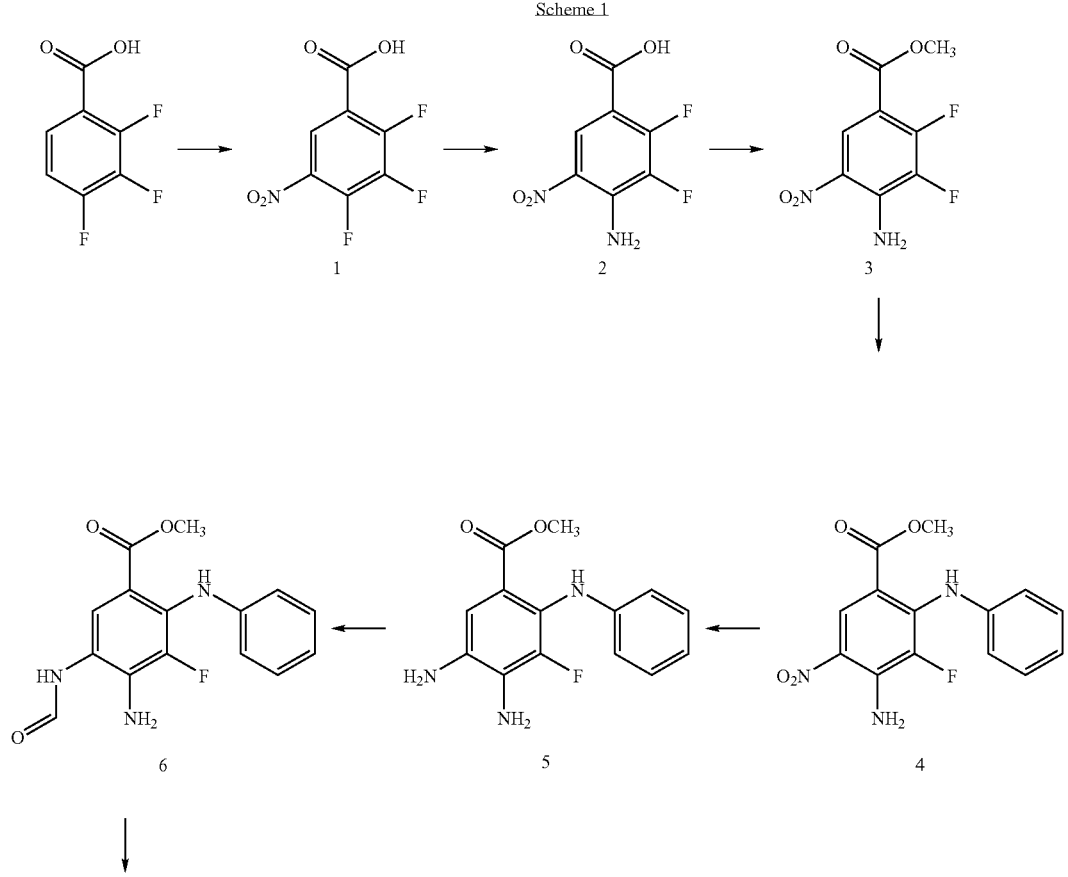

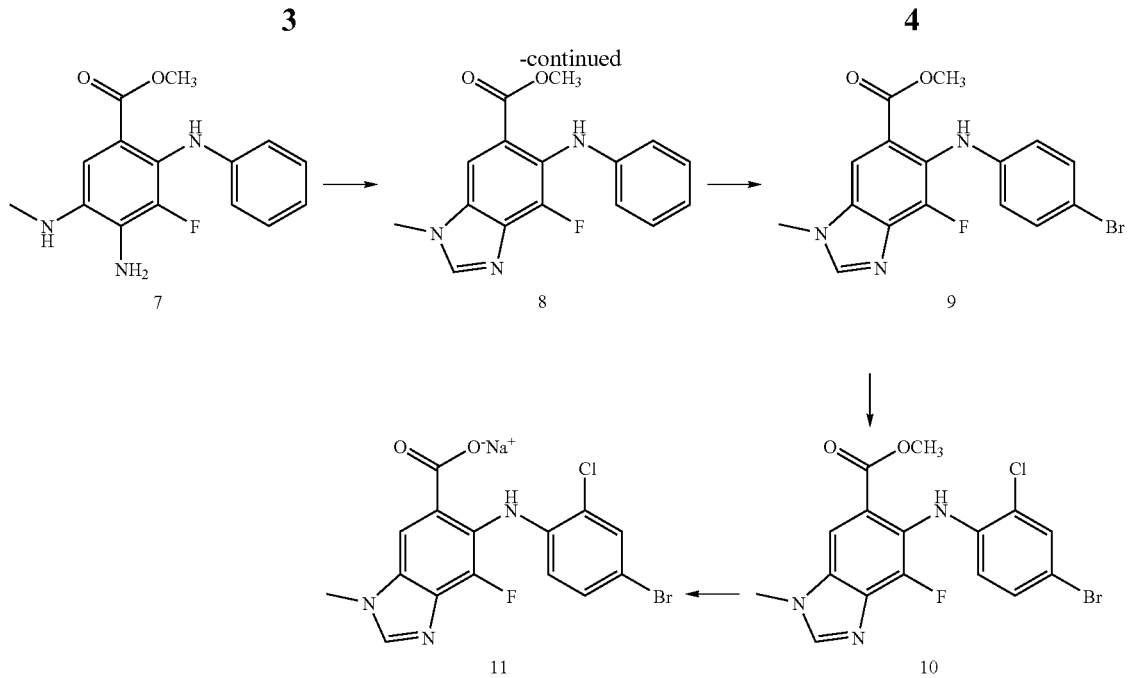

SUMMARY OF THE INVENTION

In general, the present invention provides methods for preparing heterocyclic compounds and their synthetic intermediates, which are useful for the production of therapeutic compounds such as benzimidazole derivatives.

According to one aspect of the present invention, methods are provided for the preparation of compounds of the general Formulas Ia-1, Ia-2, Ib-1, Ib-2 and their synthetic intermediates

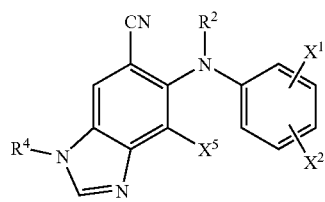

Ia-1

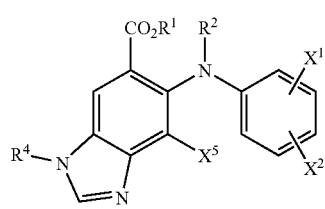

Ia-2

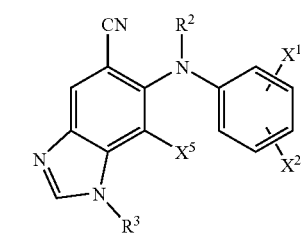

Ib-1

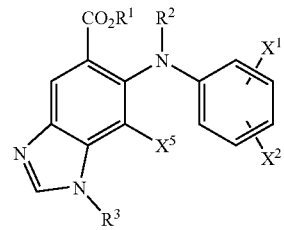

Ib-2 and salts and solvates thereof, wherein:

$R^1$ is hydrogen, $C_1$-$C_{10}$ alkyl, $C_2$-$C_{10}$ alkenyl, $C_2$-$C_{10}$ alkynyl, cycloalkyl, $C_3$-$C_{10}$ cycloalkylalkyl, aryl, arylalkyl, heteroaryl, heteroarylallyl, heterocyclyl, heterocyclylalkyl, trialkylsilyl or dialkylarylsilyl, wherein said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from halogen, hydroxyl, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl;

$R^2$ is hydrogen, $C_1$-$C_{10}$ alkyl, $C_2$-$C_{10}$ alkenyl, $C_2$-$C_{10}$ alkynyl, arylalkyl, trialkylsilyl, dialkylarylsilyl, —$COR^5$, —$C(O)OR^5$ or —$C(O)NR^5R^6$, wherein said alkyl, alkenyl, alkynyl, benzyl, allyl and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl;

$R^3$ is hydrogen, $C_1$-$C_{10}$ alkyl, $C_2$-$C_{10}$ alkenyl, $C_2$-$C_{10}$ alkynyl, benzyl, allyl, arylalkyl, trialkylsilyl, dialkylarylsilyl, —$COR^5$, —$C(O)OR^5$ or —$C(O)NR^5R^6$, wherein said alkyl, alkenyl, alkynyl, benzyl, allyl and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl, wherein for Formulas Ib-1 and Ib-2, $R^3$ is not hydrogen;

$R^4$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, arylalkyl, heteroarylalkyl or heterocyclylalkyl, wherein said alkyl, alkenyl, alkynyl, cycloalkyl, cycloalkylalkyl, arylalkyl, heteroarylalkyl and heterocyclylalkyl portions are optionally substituted with one or more groups independently selected from halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^5R^6$ and —$OR^7$;

$X^1$ and $X^2$ are independently selected from hydrogen, F, Cl, Br, I, $OR^7$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl and $C_1$-$C_{10}$ thioalkyl, wherein said alkyl, alkenyl, alkynyl, cycloalkyl, cycloalkylalkyl and thioalkyl portions are optionally substituted with one or more groups independently selected from oxo, halogen, trifluoromethyl, difluoromethoxy and trifluoromethoxy;

$X^5$ is H, F, Cl, Br, I or $C_1$-$C_6$ alkyl;

$R^5$ and $R^6$ are independently hydrogen, trifluoromethyl, —$OR^7$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, or $R^5$ and $R^6$ together with the atom to which they are attached form a 4 to 10 membered heteroaryl or heterocyclic ring, wherein said heteroaryl and heterocyclic rings are optionally substituted with one or more groups independently selected from halogen, cyano, nitro, trifluoromethyl, difluoromethoxy, trifluoromethoxy, azido and $OR^7$; and $R^7$ is hydrogen, $C_1$-$C_{10}$ alkyl, $C_2$-$C_{10}$ alkenyl, aryl or arylalkyl.

More specifically, one embodiment of the present invention provides a process, referred to herein as Method 1, for preparing N-3 benzimidazole compounds represented by Formula Ia-2 and their synthetic intermediates

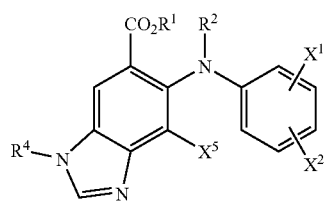

Ia-2 and salts and solvates thereof, wherein $R^1$, $R^2$, $R^4$, $X^1$, $X^2$ and $X^5$ are as defined herein, said method comprising:

reacting a compound of Formula Va or Vb

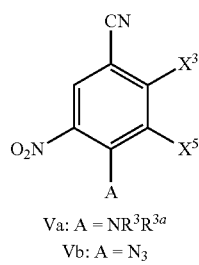

Va: A = $NR^3R^{3a}$
Vb: A = $N_3$ wherein $X^3$ is F, Cl, Br, I, or a sulfonate ester and $X^5$ and $R^3$ are as defined herein, and $R^{3a}$ is H or a group that is removable under reductive conditions such as substituted or unsubstituted benzyl, allyl or —$C(O)OR^6$, with an aniline represented by the Formula VI

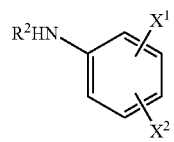

VI in the presence of a base to provide a compound having Formula VII-1a wherein A is —$NR^3R^{3a}$ or a compound of Formula VII-1b wherein A is $N_3$,

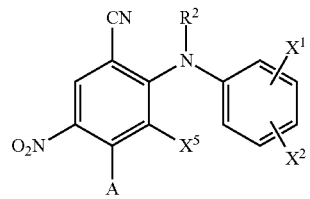

VII-1a: A = $NR^3R^{3a}$
VII-1b: A = $N_3$ wherein $R^2$, $R^3$, $R^{3a}$, $X^1$, $X^2$ and $X^5$ are as defined herein;

reducing said compound of Formula VII-1a or VII-1b to provide a compound of Formula VIII-1

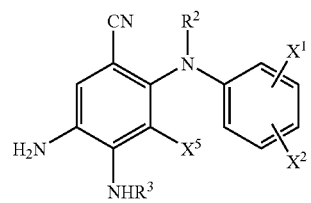

VIII-1 wherein $R^2$, $R^3$, $X^1$, $X^2$ and $X^5$ are as defined herein, wherein when A of said compound of Formula VII-1a or VII-1b is $N_3$, NH-benzyl, NH-allyl, then $NHR^3$ of said compound of Formula VIII-1 is $NH_2$;

cyclizing said compound of Formula VIII-1 to provide a compound of Formula Ia-1

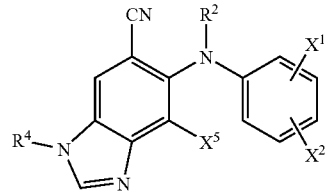

Ia-1 wherein $R^2$, $R^4$, $X^1$, $X^2$ and $X^5$ are as defined herein; and converting the nitrile group in said compound of Formula Ia-1 to $COOR^1$, optionally using (i) aqueous hydrolysis with or without an acid or base or (ii) enzymatic hydrolysis, to provide said compound of Formula Ia-2

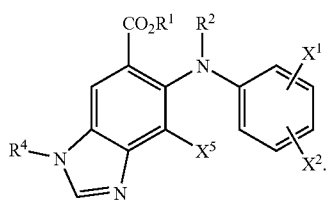

Ia-2

In one embodiment of Method 1, the compound of Formula Va or Vb is prepared according to the method comprising:
nitrating a compound having the Formula IIa

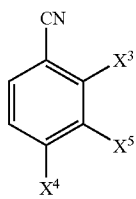

IIa wherein $X^3$ and $X^4$ are independently F, Cl, Br, I, or a sulfonate ester and $X^5$ is as defined herein to provide a compound of Formula IV

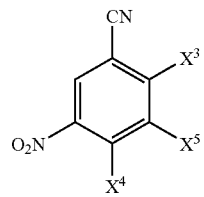

IV wherein $X^3$ and $X^4$ are as defined herein; and
reacting said compound of Formula IV with (i) a reagent that contains or generates ammonia, (ii) a primary or secondary amine other than an aromatic amine or (iii) a reagent that delivers a group that can subsequently be converted into an amine, under conditions that allow selective displacement of $X^4$ of said compound of Formula IV, to provide said compound of Formula Va wherein A is $NR^3R^{3a}$; or reacting said compound of Formula IV with (iv) a metal azide under conditions that allow selective displacement of $X^4$ of said compound of Formula IV to provide said compound of Formula Vb wherein A is $N_3$.

In another embodiment of Method 1, the compound of Formula Va or Vb is prepared by the method comprising:
nitrating a compound of Formula IIb

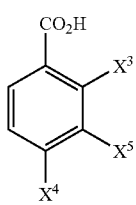

IIb wherein $X^3$ and $X^4$ are independently F, Cl, Br, I, or a sulfonate ester, and $X^5$ is as defined herein, to provide a compound of Formula III

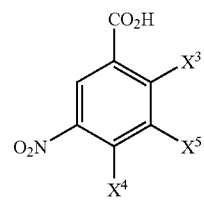

III wherein $X^3$, $X^4$ and $X^5$ are as defined herein;
converting the carboxylic acid function of said compound of Formula III to a primary amide($CONH_2$) to provide a compound of Formula IIId

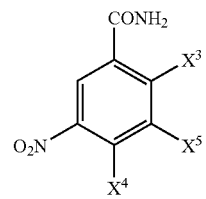

IIId dehydrating the primary amide group of said compound of Formula IIId to provide a compound of Formula IV

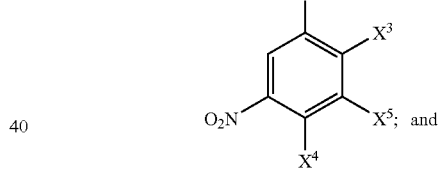

IV reacting said compound of Formula IV with (i) a reagent that contains or generates ammonia, (ii) a primary or secondary amine other than an aromatic amine or (iii) a reagent that delivers a group that can subsequently be converted into an amine, under conditions that allow selective displacement of $X^4$ of said compound of Formula IV, to provide said compound of Formula Va wherein A is $NR^3R^{3a}$; or reacting said compound of Formula IV with (iv) a metal azide under conditions that allow selective displacement of $X^4$ of said compound of Formula IV to provide said compound of Formula Vb wherein A is $N_3$.

In yet another embodiment, a compound of Formula Va or Vb is prepared by the method comprising:
nitrating a compound of Formula IIb

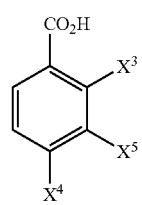

IIb wherein $X^3$ and $X^4$ are independently F, Cl, Br, I, or a sulfonate ester and $X^5$ is as defined herein, to provide a compound of Formula III

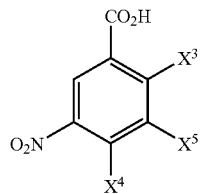

III wherein $X^3$, $X^4$ and $X^5$ are as defined herein;

reacting said compound of Formula III with (i) a reagent that contains or generates ammonia, (ii) a primary or secondary amine other than an aromatic amine or (iii) a reagent that delivers a group that can subsequently be converted into an amine, under conditions that allow selective displacement of $X^4$ of said compound of Formula III, to provide a compound of Formula IIIa-1 wherein A is $NR^3R^{3a}$; or reacting said compound of Formula III with (iv) a metal azide under conditions that allow selective displacement of $X^4$ of said compound of Formula III to provide a compound of Formula IIIa-2 wherein A is $N_3$

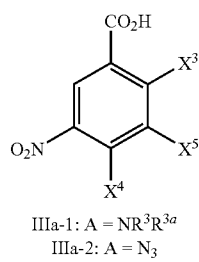

IIIa-1: A = $NR^3R^{3a}$
IIIa-2: A = $N_3$ wherein $R^3$, $R^{3a}$, $X^3$, $X^4$ and $X^5$ are as defined herein;

converting the carboxylic acid group of said compound of Formula IIIa-1 or IIIa-2 to a carboxylic acid ester to provide a compound of Formula IIIb-1 or IIIb-2, respectively,

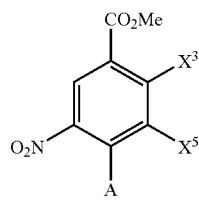

IIIb-1: A = $NR^3R^{3a}$
IIIb-2: A = $N_3$ wherein $R^3$, $R^{3a}$, $X^3$ and $X^5$ are as defined herein;

converting the carboxylic acid ester group of said compound of Formula IIIb-1 or IIIb-2 to a primary amide group to provide a compound of Formula IIIc-1 or IIIc-2, respectively,

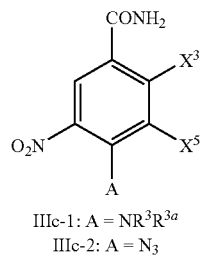

IIIc-1: A = $NR^3R^{3a}$
IIIc-2: A = $N_3$ wherein $R^3$, $R^{3a}$, $X^3$ and $X^5$ are as defined herein; and dehydrating said primary amide group of said compound of Formula IIIc-1 or IIIc-2 to provide said compound of Formula Va or Vb.

In another embodiment, the present invention provides a process, referred to herein as Method 2, for preparing N-3 benzimidazole compounds represented by Formula Ia-2 and their synthetic intermediates, said method comprising:

providing a compound of Formula VIII-1 prepared as described in Method 1

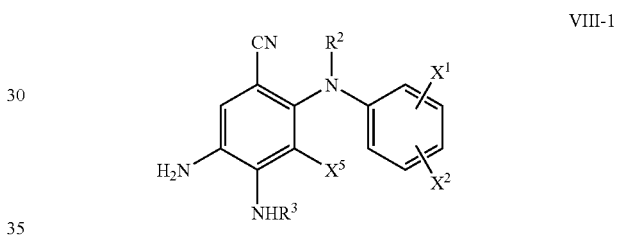

VIII-1 wherein $R^2$, $R^3$, $X^1$, $X^2$ and $X^5$ are as defined herein and wherein when A of said compound of Formula VII-1a or VII-1b is $N_3$, NH-benzyl, NH-allyl, then $NHR^3$ of said compound of Formula VIII-1 is $NH_2$;

converting the nitrile group of said compound of Formula VIII-1 to $COOR^1$, optionally using (i) aqueous hydrolysis with or without an acid or base or (ii) enzymatic hydrolysis, to provide a compound of Formula VIII-2

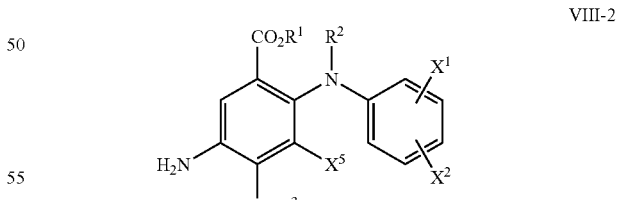

VIII-2 wherein $R^1$, $R^2$, $R^3$, $X^1$, $X^2$ and $X^5$ are as defined herein; and cyclizing said compound of Formula VIII-2 to provide said compound of Formula Ia-2.

In another embodiment, the present invention provides a process, referred to herein as Method 3, for preparing N-3 benzimidazole compounds represented by Formula Ia-2 and their synthetic intermediates, said method comprising:

providing a compound of Formula VII-1a or VII-1b, prepared as described in Method 1

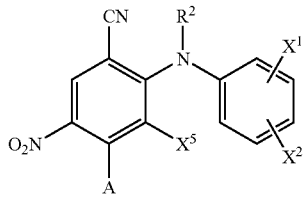

VII-1a: A = NR³R³ᵃ
VII-1b: A = N₃ wherein $R^2$, $R^3$, $R^{3a}$, $X^1$, $X^2$ and $X^5$ are as defined herein;

converting the nitrile group of said compound of Formula VII-1a or VII-1b to COOR¹, optionally using (i) aqueous hydrolysis with or without an acid or base or (ii) enzymatic hydrolysis, to provide a compound of Formula VII-2a or VII-2b

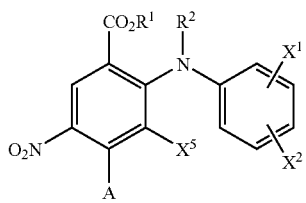

VII-2a: A = NR³R³ᵃ
VII-2b: A = N₃ wherein $R^1$, $R^2$, $R^3$, $R^{3a}$, $X^1$, $X^2$ and $X^5$ are as defined herein;

reducing said compound of Formula VII-2a or VII-2b to provide a compound of Formula

VIII-2

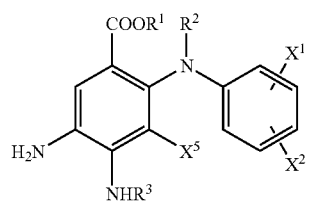

wherein $R^1$, $R^2$, $R^3$, $X^1$, $X^2$ and $X^5$ are as defined herein, wherein when A of said compound of Formula VII-2a or VII-2b is N₃, NH-benzyl, NH-allyl, then NHR³ of said compound of Formula VIII-2 is NH₂; and cyclizing said compound of Formula VIII-2 to provide said compound of Formula Ia-2.

In yet another embodiment, the present invention provides a process, referred to herein as Method 4, for preparing N-1 benzimidazole compounds represented by Formula Ib-2 and their synthetic intermediates

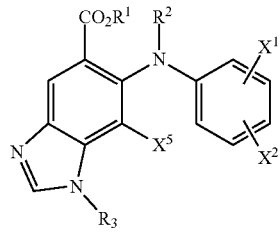

Ib-2 and salts and solvates thereof, wherein $R^1$, $R^2$, $R^3$, $X^1$, $X^2$ and $X^5$ are as defined herein, with the proviso that $R^3$ is not hydrogen, said method comprising:

providing a compound of Formula prepared as described in Method 1

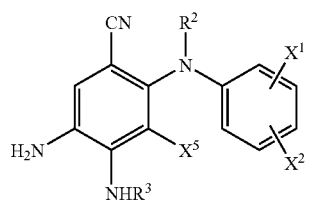

VIII-1 wherein $R^2$, $R^3$, $X^1$, $X^2$ and $X^5$ are as defined herein, with the proviso that $R^3$ is not hydrogen and wherein when A of said compound of Formula VII-1a or VII-1b is N₃, NH-benzyl, NH-allyl, then NHR³ of said compound of Formula VIII-1 is NH₂;

cyclizing said compound of Formula VIII-1 to provide a compound of Formula Ib-1

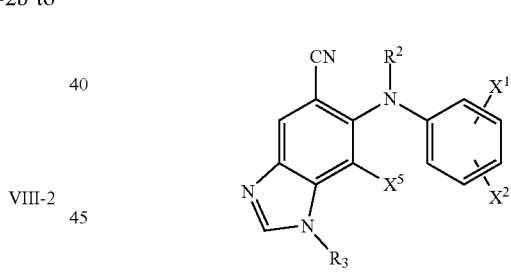

Ib-1 wherein $R^2$, $R^3 X^1$, $X^2$ and $X^5$ are as defined herein; and and converting of the nitrile group in Ib-1 to COOR¹, optionally using (i) aqueous hydrolysis with or without an acid or base or (ii) enzymatic hydrolysis, to provide said compound of Formula Ib-2

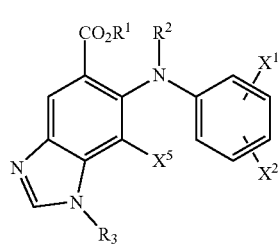

Ib-2 wherein $R^1$, $R^2$, $R^3 X^1$, $X^2$ and $X^5$ are as defined herein.

In one embodiment the cyclization Method A described below can be used in conjunction with Method 4 above.

The step of cyclizing a compound of Formula or to provide the benzimidazole core structures in any of the above-described Methods 1-4 can be performed in several ways. Five cyclization methods, namely Methods A-E, are described in general below with respect to the cyclization of a compound of Formula VIII-1. However, it is to be understood that Methods A-E apply equally to the cyclizations of compounds of Formulas VIII-2. The cyclization methods will provide either N-3 benzimidazole derivatives or N-1 benzimidazole derivatives, depending on the reagents used and the particular $R^3$ substituents on the compounds of Formulas Method A: A compound of Formula wherein $R^3$ is hydrogen, can be cyclized to the corresponding benzimidazole represented by Formula Ia-1, wherein $R^4$ is hydrogen, by a "one pot" method upon treatment with (i) formic acid, optionally in the presence of a second acid or (ii) a formic acid derivative in the presence of an acid. The nitrile group of said compound of Formula Ia-1 can then be converted to a $COOR^1$ group, wherein $R^1$ is as defined herein, to provide of the benzimidazole tautomer represented by Formula Ia-2 wherein $R^4$ is hydrogen. If desired, the compound of Formula Ia-2 can be reacted with an alkylating agent to provide a mixture of the N-1 and N-3 alkylated benzimidazoles Ia-2 and Ib-2

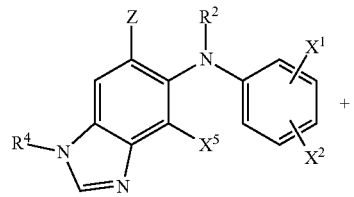

Ia-2

+

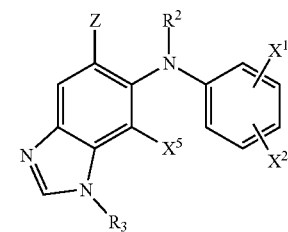

Ib-2 wherein $R^4$ and $R^3$ are not hydrogen.

Method B: A compound of Formula VIII-1, wherein $R^3$ is not hydrogen, can be cyclized to the corresponding N-1 benzimidazole represented by Formula Ib-1 by a "one pot" method upon treatment with (i) formic acid, optionally in the presence of a second acid, (ii) a formic acid derivative in the presence of an acid, or (iii) formaldehyde or a formaldehyde derivative in the presence of an acid. The nitrile group of said compound of Formula Ib-1 can then be converted to a $COOR^1$ group, wherein $R^1$ is as defined herein, to provide a compound of Formula Ib-2.

Method C: A compound of Formula VIII-1, wherein $R^3$ is hydrogen, can be cyclized to the corresponding N-3 benzimidazole represented by Formula Ia-1 wherein $R^4$ is methyl, by a "one pot" method upon treatment with two or more equivalents of formaldehyde or a formaldehyde derivative in the presence of an acid. The nitrile group of said compound of Formula Ia-1 can then be converted to a $COOR^1$ group, wherein $R^1$ is as defined herein, to provide a compound of Formula Ia-2.

Method D: A compound of Formula VIII-1, wherein $R^3$ is hydrogen, can be cyclized to the corresponding benzimidazole represented by Formula Ib-1 wherein $R^4$ is not hydrogen, by a step-wise process comprising:

(a) (i) reacting a compound of Formula VIII-1

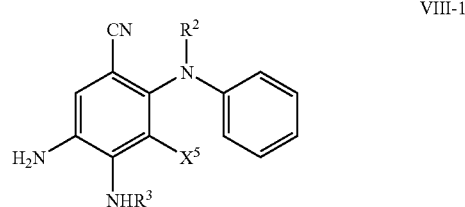

VIII-1 with an acylating agent to provide a compound of Formula IX-1

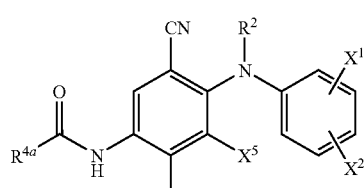

IX-1 wherein $R^2$, $R^3$, $X^1$, $X^2$, $X^5$ are as defined herein and $R^{4a}$ is H, $C_1$-$C_{10}$ alkyl, $C_3$-$C_{10}$ cycloalkylalkyl, arylalkyl, heteroarylalkyl or heterocyclylalkyl, and (ii) reducing the amide group of said compound of Formula IX-1 to provide a compound of Formula X-1

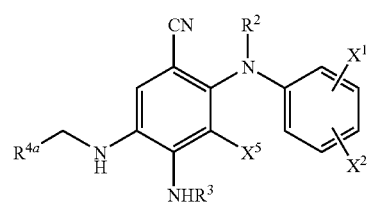

X-1 wherein $R^2$, $R^3$, $R^{4a}$, $X^1$, $X^2$, $X^5$ are as defined herein; or (b) reacting said compound of Formula VIII-1 with an alkylating agent to provide said compound of Formula X-1; and (c) reacting said compound of Formula X-1 with (i) formic acid optionally in the presence of a second acid or (ii) a formic acid derivative in the presence of a second acid to provide said compound of Formula Ia-1. The nitrile group of said compound of Formula Ia-1 can then be converted to a $COOR^1$ group, wherein $R^1$ is as defined herein, to provide a compound of Formula Ia-2.

Method E: A compound of Formula VIII-1, where $R^3$ is not hydrogen, can be cyclized to the corresponding benzimidazole compound of Formula XI-1, wherein $R^4$ is not hydrogen, by a step-wise method comprising:

(a) (i) reacting a compound of Formula VIII-1

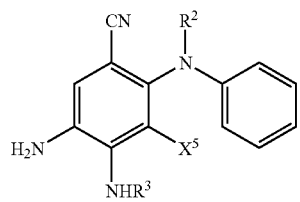

VIII-1 with a suitable acylating agent to provide a compound of Formula IX-1

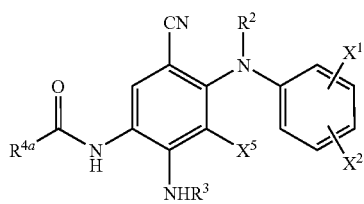

IX-1 wherein $R^2$, $R^3$, $X^1$, $X^2$, $X^5$ are as defined herein and $R^{4a}$ is H, $C_1$-$C_{10}$ alkyl, $C_3$-$C_{10}$ cycloalkylalkyl, arylalkyl, heteroarylalkyl or heterocyclylalkyl; and (ii) reducing the amide group of said compound of Formula IX-1 to provide a compound of Formula X-1

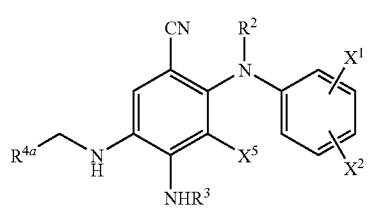

X-1 wherein $R^2$, $R^3$, $R^{4a}$, $X^1$, $X^2$, $X^5$ are as defined herein; or
(b) reacting said compound of Formula VIII-1 with an alkylating agent to provide said compound of Formula X-1;
(c) reacting said compound of Formula X-1 with (i) formic acid optionally in the presence of a second acid or (ii) a formic acid derivative in the presence of a second acid to provide said compound of Formula XI-1

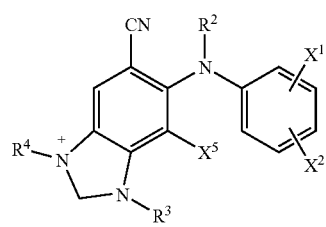

XI-1 wherein $R^2$, $R^3$, $R^4$, $X^1$, $X^2$, $X^5$ and $X^5$ are as defined herein; and
removing the $R^3$ group to provide the N-3 benzimidazole compound of Formula Ia-1. The nitrile group of said compound of Formula Ia-1 can then be converted to a $COOR^1$ group, wherein $R^1$ is as defined herein, to provide a compound of Formula Ia-2.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the detailed description and in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

DETAILED DESCRIPTION OF THE INVENTION

Figure 1:
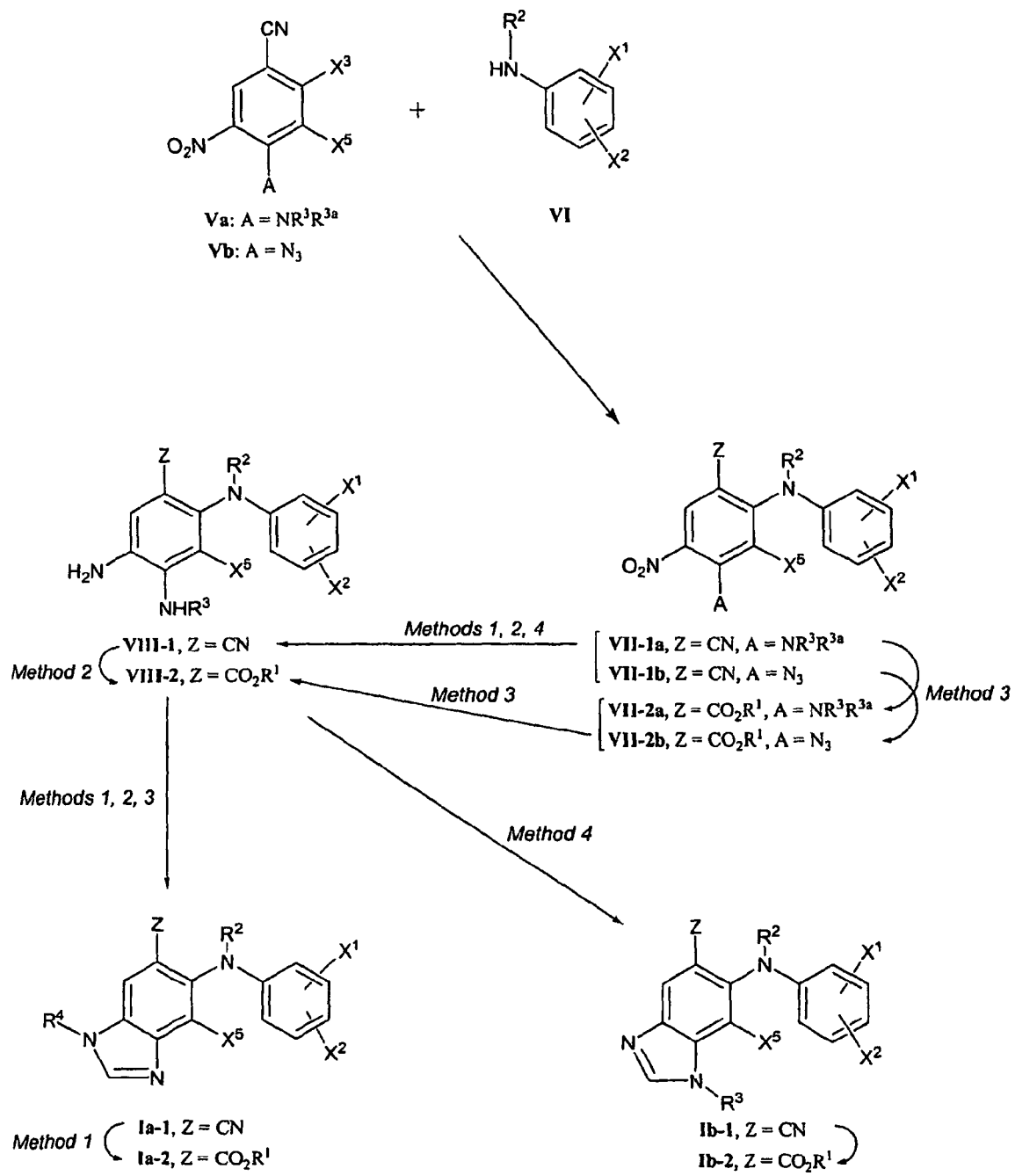
FIG. 1 shows a reaction scheme (Methods 1-4) for the synthesis of compounds having the Formula Ia-1, Ia-2, Ib-1 and Ib-2 and their synthetic intermediates.

One aspect of the present invention provides methods for the preparation of compounds of the general Formulas Ia-1, Ia-2, Ib-1 and Ib-2 and their synthetic intermediates

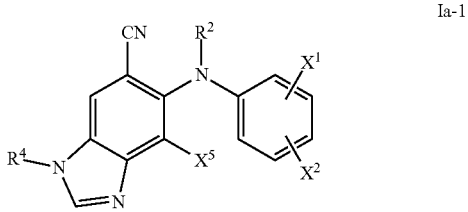

Ia-1

-continued

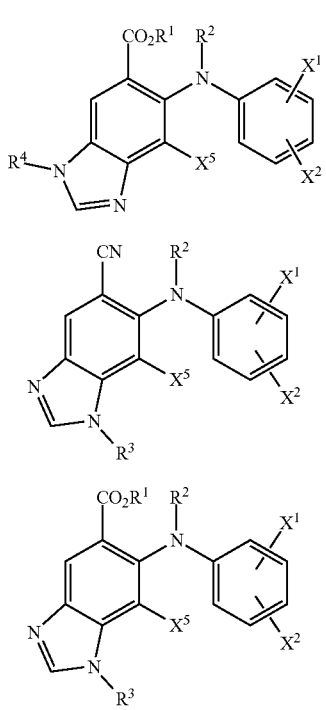

Ia-2

Ib-1

Ib-2 and salts and solvates thereof, wherein:

$R^1$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, trialkylsilyl or dialkylarylsilyl, wherein said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from halogen, hydroxyl, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl;

$R^2$ is hydrogen, $C_1$-$C_{10}$ alkyl, $C_2$-$C_{10}$ alkenyl, $C_2$-$C_{10}$ alkynyl, arylalkyl, trialkylsilyl, dialkylarylsilyl, —$COR^5$, —C(O)$OR^5$ or —C(O)$NR^5R^6$, wherein said alkyl, alkenyl, alkynyl, benzyl, allyl and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl;

$R^3$ is hydrogen, $C_1$-$C_{10}$ alkyl, $C_2$-$C_{10}$ alkenyl, $C_2$-$C_{10}$ alkynyl, benzyl, allyl, arylalkyl, trialkylsilyl, dialkylarylsilyl, —$COR^5$, —C(O)$OR^5$ or —C(O)$NR^5R^6$, wherein said alkyl, alkenyl, alkynyl, benzyl, allyl and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl, wherein for Formulas Ib-1 and Ib-2, $R^3$ is not hydrogen;

$R^4$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, arylalkyl, heteroarylalkyl or heterocyclylalkyl, wherein said alkyl, alkenyl, alkynyl, cycloalkyl, cycloalkylalkyl, arylalkyl, heteroarylalkyl and heterocyclylalkyl portions are optionally substituted with one or more groups independently selected from halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^5R^6$ and —$OR^7$;

$X^1$ and $X^2$ are independently selected from hydrogen, F, Cl, Br, I, $OR^7$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl and $C_1$-$C_{10}$ thioalkyl, wherein said alkyl, alkenyl, alkynyl, cycloalkyl, cycloalkylalkyl and thioalkyl portions are optionally substituted with one or more groups independently selected from oxo, halogen, trifluoromethyl, difluoromethoxy and trifluoromethoxy;

$X^5$ is H, F, Cl, Br, I or $C_1$-$C_6$ alkyl;

$R^5$ and $R^6$ are independently hydrogen, trifluoromethyl, —$OR^7$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, or $R^5$ and $R^6$ together with the atom to which they are attached form a 4 to 10 membered heteroaryl or heterocyclic ring, wherein said heteroaryl and heterocyclic rings are optionally substituted with one or more groups independently selected from halogen, cyano, nitro, trifluoromethyl, difluoromethoxy, trifluoromethoxy, azido and $OR^7$; and $R^7$ is hydrogen, $C_1$-$C_{10}$ alkyl, $C_2$-$C_{10}$ alkenyl, aryl or arylalkyl.

Methods for preparing N-3 benzimidazole compounds of the general Formulas Ia-1, Ia-2, Ib-1 and Ib-2 can be performed in several ways and are described below. Three methods, namely Methods 1-3, for preparing the N-3 benzimidazole compounds of the general Formulas Ia-1 and Ia-2 are shown in FIG. 1. Method 4, also shown in FIG. 1, describes the synthesis of the N-1 benzimidazole derivatives represented by Formulas Ib-1 and Ib-2.

In certain embodiments of Methods 1-4, $X^5$ is halogen. In other embodiments, $X^5$ is F. In yet another embodiment, $X^1$ is H or halogen. In another embodiment $X^2$ is alkyl or halogen. In one embodiment $X^2$ is Br.

In certain embodiments of Methods 1-4, $R^4$ is $C_1$-$C_{10}$ alkyl. In particular embodiments, $R^4$ is methyl.

In some embodiments of Methods 1-4, $R^2$ is hydrogen.

Method 1: One embodiment of the present invention provides a method, referred to herein as Method 1 and shown schematically in FIG. 1, for preparing compounds of Formulas Ia-1 and Ia-2 and their synthetic intermediates

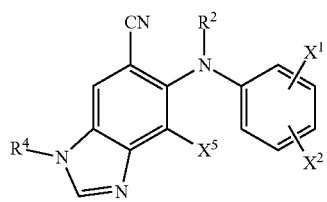

Ia-1

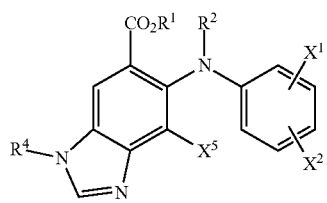

Ia-2 and salts and solvates thereof, wherein $R^2$, $R^4$, $X^1$, $X^2$ and $X^5$ are as defined herein.

More specifically, Method 1, as shown in FIG. 1, comprises preparation of a compound of Formula Ia-1 or Ia-2 from a compound of Formula Va or Vb

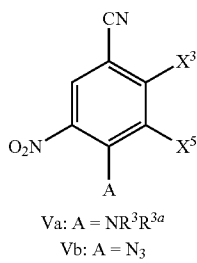

Va: A = NR³R³ᵃ
Vb: A = N₃ wherein $X^3$ is F, Cl, Br, I or a sulfonate ester such as, but not limited to, trifluoromethanesulfonate, methanesulfonate, benzenesulfonate or p-toluenesulfonate, $R^{3a}$ is H or a group that is removable under reductive conditions such as substituted or unsubstituted benzyl, allyl or —C(O)OR⁶, and $X^5$ and $R^3$ are defined herein.

Figure 2:
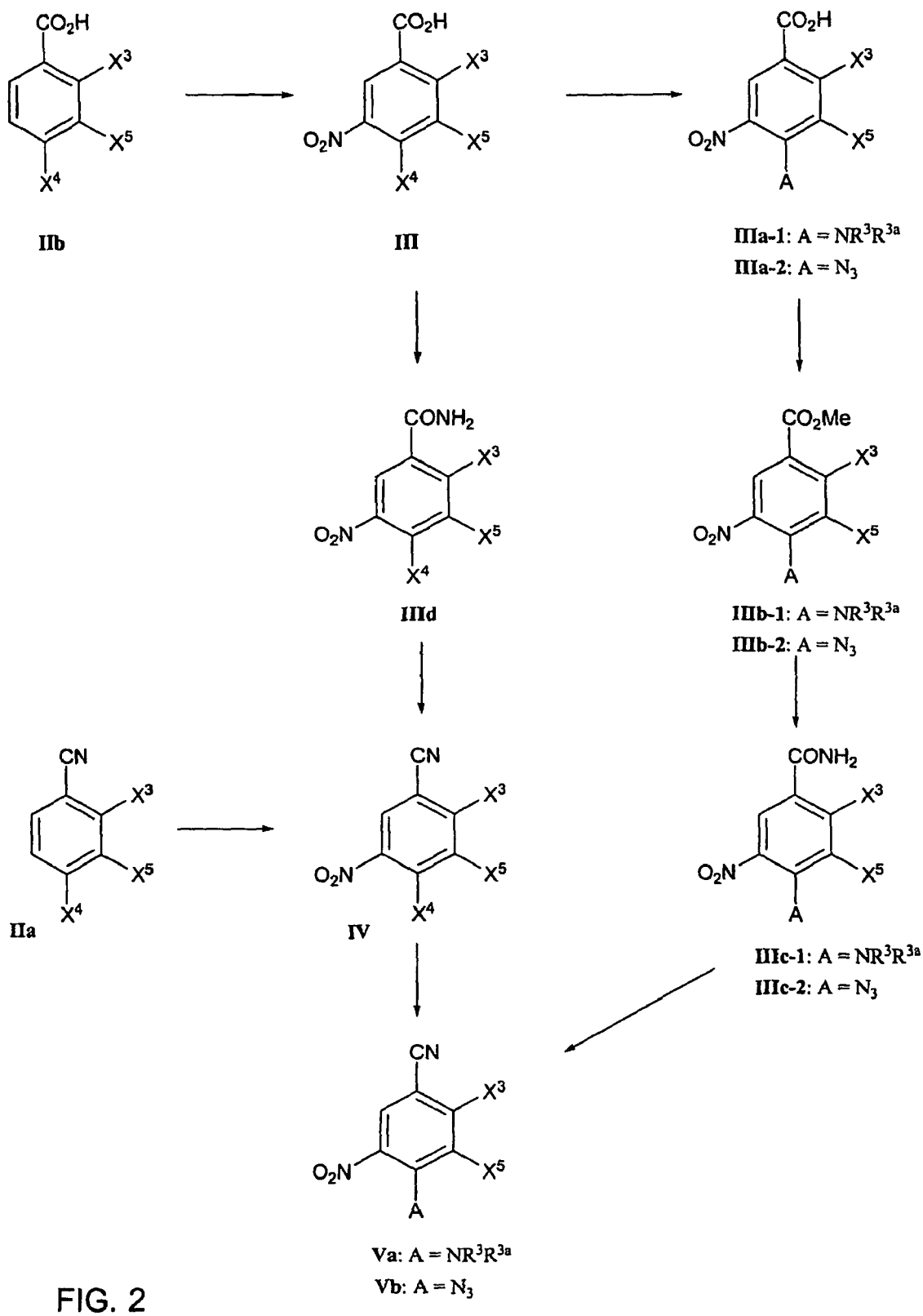
FIG. 2 shows several synthetic routes for preparing the intermediate compounds represented by Formulas Va and Vb.

A compound of Formula Va or Vb can be prepared by several methods as shown in FIG. 2. For example, according to one embodiment a compound of Formula Va or Vb is prepared by the method comprising:

nitrating a compound of Formula IIa

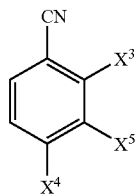

IIa wherein $X^3$ and $X^4$ are independently F, Cl, Br, I, or a sulfonate ester and $X^5$ is as defined herein to provide a compound of Formula IV

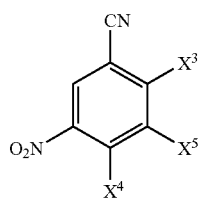

IV wherein $X^3$, $X^4$ and $X^5$ are as defined herein. In one embodiment, $X^3$, $X^4$ and $X^5$ are F. The compound of Formula IV is then reacted with (i) a reagent that contains or generates ammonia, (ii) a primary or secondary amine other than an aromatic amine, or (iii) a reagent that delivers a group that can subsequently be converted into an amine, under conditions that allow selective displacement of $X^4$ of said compound of Formula IV, to provide said compound of Formula Va wherein A is NR³R³ᵃ; or said compound of Formula IV is reacted with (iv) a metal azide under conditions that allow selective displacement of $X^4$ of said compound of Formula IV to provide said compound of Formula Vb wherein A is N₃.

Nitration reaction conditions suitable for the preparation of compounds of Formula IV are well known to those skilled in the art, and include, but are not limited to reacting a compound of Formula IIa with nitric acid in the presence of an activating agent such as concentrated sulfuric acid.

With continued reference to FIG. 2, the $X^4$ group of the compound of Formula IV is then selectively replaced by a nitrogen nucleophile to provide a compound of Formula Va or Vb. Examples of nucleophilic reagents that contain or generate ammonia include, but are not limited to, NH₃ and NH₄OH. Examples of nucleophilic primary and secondary amines include amines having the formula HNR³R³ᵃ, wherein $R^3$ and $R^{3a}$ are as defined herein. Specific examples of primary and secondary amines include, but are not limited to methylamine, benzylamine, dibenzylamine, allylamine, diallylamine and hexamethyldisilazane. Examples of nucleophilic reagents that deliver a group that can subsequently be converted into an amine include, but are not limited to, (1) metal amides such as sodium, potassium and lithium amide, or alkylated derivatives thereof, (2) protected ammonia or amide equivalents such as, but not limited to, hydroxylamines and hydrazines, (3) nitrogen nucleophiles having the Formula MNR³R³ᵃ wherein M is a metal such as Na, K, Li, Cs, Mg or Al and $R^3$ and $R^{3a}$ are as hereinbefore defined and such as NaNH₂, KNH₂ or LiNH₂ and (4) metal silylamides such as lithium (bis)(trimethylsilyl)amide, sodium (bis)(trimethylsilyl)amide or potassium (bis)(trimethylsilyl)amide. Examples of nucleophilic metal azides include, but are not limited to, sodium azide (NaN₃), potassium azide (KN₃) and lithium azide (LiN₃).

Nucleophilic substitution of a leaving group ortho- or para- to a nitro group in an aromatic ring is a method well known in the art for the introduction of an amino group into an aromatic ring. In the case of compounds of Formula IV, it was discovered that, under controlled reaction conditions, the leaving groups $X^3$ and $X^4$ can be replaced independently in separate steps. That is, the group in the position ortho- to the nitro group in compounds of Formula IV (i.e., the $X^4$ group) is selectively replaced by a nitrogen nucleophile with minimal or no displacement of the $X^3$ group when the reaction is performed under the appropriate reaction conditions. The reaction conditions (e.g., temperature, pressure, equivalents of nucleophile, etc.) needed to achieve selective mono-amination at the position ortho- to the nitro group of compound of Formula IV depend on the strength of the nucleophile. For example, if a strong nucleophile is used, the reaction may proceed easily at or below room temperature and at atmospheric pressure using one equivalent of the nucleophile to provide the desired mono-amination product. Examples of strong nucleophiles include, but are not limited to, aqueous ammonia (30% vol/vol) and metal amides such as sodium, potassium and lithium amide. Alternatively, if a weak nucleophile is used, more forcing conditions such as elevated temperatures and/or elevated pressure and/or an excess amount of the nucleophile may be required to achieve monoamination. Examples of weak nucleophiles include, but are not limited to, a primary or secondary amine substituted with a sterically bulky group such as t-butyl. The introduction of an amino group at the position ortho- to the nitro group provides the substitution product represented by Formula Va or Vb, which is less reactive to further nucleophilic attack, and therefore the reaction can be carried out with a high level of selectivity. The leaving group $X^3$ at the position para- to the nitro group is replaced in a subsequent step of Method 1 by an aniline nucleophile. The discovery of methodology that allows the two substitution reactions to be carried out selectively and independently allows for an efficient route for the manufacture of substituted benzimidazoles of a type represented by 1a-1 and 1a-2.

In a particular embodiment, a compound of Formula Va is prepared by reacting a compound of Formula IV with excess NH₄OH at room temperature in water (with or without an organic co-solvent). Examples of suitable organic co-solvents include THF, 1,4-dioxane and N-methylpyrrolidine. Alternatively, a compound of Formula Va can be prepared by reacting a compound of Formula IV with aqueous ammonia at temperatures between 0 and 130° C., in particular between 30 and 130° C. under 1-5 bar $NH_{3(g)}$. In one embodiment, a compound of Formula IV is reacted with aqueous ammonia at temperatures between 0° C. and room temperature. In another embodiment, a compound of Formula IV is reacted with aqueous ammonia under 1 bar $NH_{3(g)}$.

According to another embodiment as shown in FIG. 2, a compound of Formula Va or Vb is prepared by the method comprising:

nitrating a compound of Formula IIb

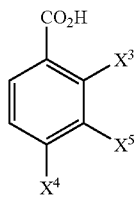

wherein $X^3$, $X^4$ and $X^5$ are as defined herein, to provide a compound of Formula III

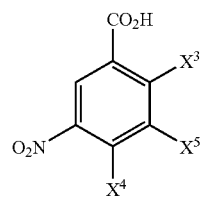

wherein $X^3$, $X^4$ and $X^5$ are as defined herein;

converting the carboxylic acid group of said compound of Formula III to a primary amide group under stander conditions well known to persons skilled in the art (for example, by treating a compound of Formula III with concentrated aqueous ammonium hydroxide at room temperature) to provide a compound of Formula IIId

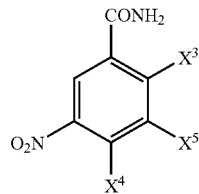

wherein $X^3$, $X^4$ and $X^5$ are as defined herein; and dehydrating the primary amide group of said compound of Formula IIId under standard dehydration conditions well known to persons skilled in the art to provide a compound of Formula IV

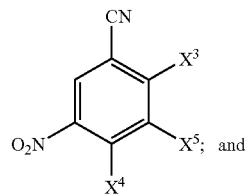

reacting said compound of Formula IV with (i) a reagent that contains or generates ammonia, (ii) a primary or secondary amine other than an aromatic amine or (iii) a reagent that delivers a group that can subsequently be converted into an amine, under conditions that allow selective displacement of $X^4$ of said compound of Formula IV, to provide said compound of Formula Va wherein A is $NR^3R^{3a}$; or reacting said compound of Formula IV with (iv) a metal azide under conditions that allow selective displacement of $X^4$ of said compound of Formula IV to provide said compound of Formula Vb wherein A is $N_3$. For example, in one embodiment a compound of Formula IIId wherein $X^3=X^4=X^5=F$, can be treated with $POCl_3$ at a temperature above ambient and in a suitable solvent such as, but not limited to acetonitrile, to provide the compound of Formula IV.

The nitration conditions for preparing a compound of Formula III are as described above. For example, in one embodiment a trihalobenzoic represented by Formula IIb can be treated with fuming nitric acid in $H_2SO_4$ to provide a 2,3,4-trihalo-5-nitrobenzoic acid represented by Formula III in high yield.

In yet another embodiment as shown in FIG. 2, a compound of Formula Va or Vb is prepared by the method comprising:

nitrating a compound of Formula IIb

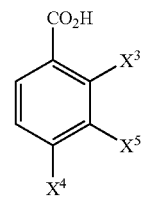

wherein $X^3$, $X^4$ and $X^5$ are as defined herein, to provide a compound of Formula III

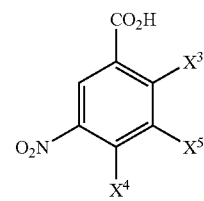

wherein $X^3$, $X^4$ and $X^5$ are as defined herein;

reacting said compound of Formula III with (i) a reagent that contains or generates ammonia, (ii) a primary or secondary amine other than an aromatic amine or (iii) a reagent that delivers a group that can subsequently be converted into an amine, under conditions that allow selective displacement of $X^4$ of said compound of Formula III, to provide a compound of Formula IIIa-1 wherein A is $NR^3R^{3a}$; or reacting said compound of Formula III with (iv) a metal azide under conditions that allow selective displacement of $X^4$ of said compound of Formula III to provide a compound of Formula IIa-2 wherein A is $N_3$

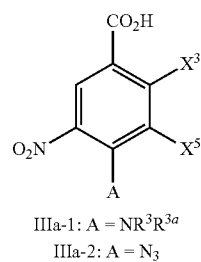

IIIa-1: A = $NR^3R^{3a}$
IIIa-2: A = $N_3$ converting the carboxylic acid group of said compound of Formula IIIa-1 or IIIa-2 to a carboxylic acid ester under stander conditions well known to persons skilled in the art to provide a compound of Formula IIIb-1 or IIIb-2, respectively,

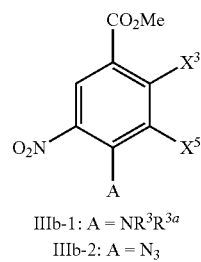

IIIb-1: A = $NR^3R^{3a}$
IIIb-2: A = $N_3$ wherein $R^3$, $R^{3a}$, $X^3$ and $X^5$ are as defined herein;

converting the carboxylic acid ester group of said compound of Formula IIIb-1 or IIIb-2 to a primary amide group under stander conditions well known to persons skilled in the art to provide a compound of Formula IIIc-1 or IIIc-2, respectively,

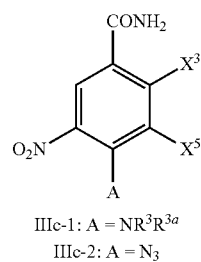

IIIc-1: A = $NR^3R^{3a}$
IIIc-2: A = $N_3$ wherein $R^3$, $R^{3a}$, $X^3$ and $X^5$ are as defined herein; and dehydrating said primary amide group of said compound of Formula IIIc-1 or IIIc-2 under stander conditions well known to persons skilled in the art to provide said compound of Formula Va or Vb.

This invention further provides compounds of Formula Va and Vb salts and solvates thereof. In one embodiment of a compound of Formula Va, $X^3$ and $X^5$ are F, and $R^3$ and $R^{3a}$ are H.

With continued reference to FIG. 1, a compound of Formula VII-1a or VII-1b

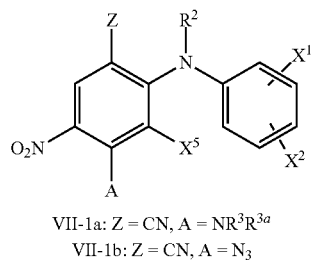

VII-1a: Z = CN, A = $NR^3R^{3a}$
VII-1b: Z = CN, A = $N_3$ wherein $X^1$, $X^2$, $X^5 R^2$, $R^3$, $R^{3a}$, A and Z are as defined herein, is then prepared by reacting a compound of Formula Va or Vb, respectively, with a substituted or unsubstituted aniline. More specifically, one embodiment for the preparation of compounds of Formula VII-1a according to Method 1 comprises a nucleophilic aromatic substitution ($S_NAr$) reaction between a compound of Formula Va or Vb and an aniline having the Formula VI

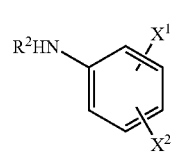

VI wherein $X^1$, $X^2$ and $R^2$ are as defined herein, in the presence of a suitable base in an appropriate solvent. The nitrile moiety in said compound of Formula Va/Vb was found to be a more effective activating substituent for this nucleophilic substitution reaction compared to an ester group in the same position.

The $S_NAr$ reaction is performed in the presence of a base that strong enough to deprotonate the aniline substrate in order to achieve effective conversion to the coupled compound VII-1a. Examples of bases that can generate reactive nucleophilic anilines include, but are not limited to: metal hydrides, such as sodium hydride; dialkyl metal amides, such as lithium dialkyl amines (e.g., lithium diisopropylamide); metal silazides, such as hexaalkyldisilazides (e.g., sodium hexamethyl disilazide, lithium hexamethyl disilazide or potassium hexamethyl disilazide); metal alkoxides, such as potassium, sodium or lithium alkoxides derived from primary secondary or tertiary alcohols (e.g., potassium tert-butoxide, sodium isoamylate); metal amides (e.g., sodium amide, potassium amide, lithium amide); Grignard reagents (e.g., alkyl magnesium halides); and aluminum reagents, such as trialkylaluminum reagents.

According to one embodiment of the invention, a compound of Formula VII-1a or VII-1b can be prepared as shown in FIG. 1 by reacting a compound of Formula Va or Vb with an aniline of Formula VI in an aprotic organic solvent in the presence of a base at a temperature between −50 and 80° C. Examples of suitable organic solvents include, but are not limited to THF, diethylether and N-methylpyrrolidine. In one embodiment, the aniline has the Formula VI

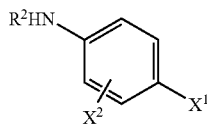

wherein $X^1$, $X^2$ and $R^2$ are as defined herein. In a particular embodiment, $X^1$ is Br. In another embodiment, a compound of Formula Va, wherein $R^3$ and $R^{3a}$ are hydrogen and $X^3$ and $X^5$ are F, is reacted with a compound of Formula VI, wherein said compound of Formula VI is 4-bromo-2-chloroaniline, in the presence of a base, for example potassium tert-butoxide, in THF at a temperature between −10 to 50° C., to provide a compound of Formula VII-1a wherein $R^3$ and $R^{3a}$ are hydrogen, $X^5$ is F, $X^1$ is 2-chloro and $X^2$ is 4-bromo.

This invention further provides compounds of Formula VII-1a and VII-1b

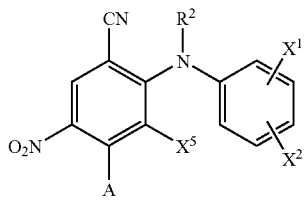

VII-1a: A = $NR^3R^{3a}$
VII-1b: A = $N_3$ and salts and solvates thereof. In one embodiment of a compound of Formula VII-1a, $X^5$ is F, and $R^2$, $R^3$ and $R^{3a}$ are H.

With continued reference to FIG. 1, the nitro group of the compound of Formula or VII-1b is then reduced to provide a compound of Formula VIII-1. The reduction step can be performed utilizing reaction conditions and reagents well known to those skilled in the art. Examples of suitable methods for reducing an aromatic nitro group include, but are not limited to, dissolving metal reductions, catalytic hydrogenations, and enzymatic reactions. More specific examples of dissolving metal reductions include the use of a metal in a suitable solvent under acidic conditions. Example of metals suitable for dissolving metal reductions include, but are not limited to, Zn, Fe and Sn. For example, in one embodiment a compound of Formula VII-1a can be converted to a compound of Formula VIII-1 using zinc powder and concentrated HCl in suitable solvent system at temperatures between 0-100° C., more typically at 40 to 60° C. Suitable solvent systems for dissolving metal reductions include organic solvent systems such as, but not limited to, a mixture of methanol and THF. Catalytic hydrogenations can be performed with hydrogen in the presence of a metal catalyst in a suitable solvent system under hydrogen (for example, 1-20 atm. $H_2$) at 0-100° C. Suitable metal catalysts for use in catalytic hydrogenations include, but are not limited to, Pd, Pt, Rh and Ni. Examples of suitable solvent systems include, but are not limited to, an organic solvent and/or aqueous organic solvents, such as a mixture of isopropanol and THF. Catalytic hydrogenation can also be performed in an organic solvent in the presence of a palladium or platinum-based catalyst (such as, but not limited to, palladium or platinum metal supported on carbon) at hydrogen pressures greater than 60 psi. In one embodiment, catalytic hydrogenation was found to be particularly effective to achieve the conversion of a compound of Formula VII-1a into a compound of Formula VIII-1.

This invention further provides compounds of Formula and salts and solvates thereof. In one embodiment of a compound of Formula VIII-1, $X^5$ is F, and $R^2$, $R^3$ and $R^{3a}$ are H.

With continued reference to FIG. 1, the compound of Formula VIII-1 can be cyclized to the benzimidazole derivative represented by Formula Ia-1

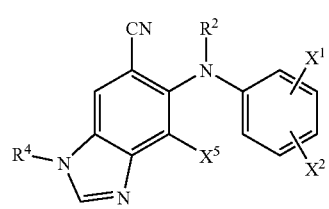

wherein $X^1$, $X^2$, $X^5$, $R^2$ and $R^4$ are as defined herein. The cyclization step to provide the benzimidazole core structure Ia-1 can be performed in several ways, such as any one of Methods A, C or D as described later in detail.

Also provided herein are compounds of Formula Ia-1 and salts and solvates thereof.

The nitrile derivative represented by Formula Ia-1 can be converted to a $COOR^1$ group, wherein $R^1$ is as defined herein, to provide a carboxyl derivative represented by Formula Ia-2

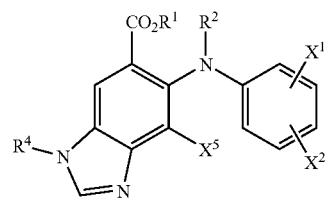

wherein $R^1$, $R^2$, $R^4$, $X^1$, $X^2$ and $X^5$ are as defined herein. Procedures for the hydrolysis or alcholysis of nitriles to carboxylic acids or esters, such as chemical or enzymatic methods, are well known to those skilled in the art. For example, chemical methods of converting a nitrile to a $COOR^1$ group include hydrolysis in water, with or without an organic co-solvent, and in the presence of an acid or base. Suitable bases include, but are not limited to, Group I or Group II metal hydroxides, carbonates and bicarbonates, such as sodium hydroxide, potassium hydroxide, lithium hydroxide, etc. Examples of suitable acids include, but are not limited to, mineral acids, for example hydrochloric acid, sulfuric acid, etc. In one embodiment the hydrolysis of the nitrile group of Formula Ia-1 to provide a compound of Formula Ia-2, wherein $R^1$ is H, is carried out using a base such as potassium hydroxide in water, with or without an organic co-solvent such as THF.

As an alternative to chemical hydrolysis, enzymes are also available that will hydrolyze the nitrile group of a compound of Formula Ia-1 into a carboxylic acid to provide a compound of Formula Ia-2. Examples of such enzymes include that will convert a nitrile group directly to a carboxylic acid include, but are not limited to, nitrilases.

Method 2: In yet another embodiment, the present invention provides a method, referred to herein as Method 2, for preparing compounds of Formula Ia-2 and their synthetic intermediates

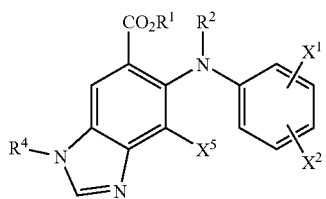

Ia-2 and salts and solvates thereof, wherein $R^1$, $R^2$, $R^4$, $X^1$, $X^2$ and $X^5$ are as defined herein. Method 2, as illustrated in FIG. 1, follows the $S_NAr$ route of Method 1, with the exception that the CN group is converted into $COOR^1$ at an earlier stage in the synthetic route. In particular, according to Method 2, a compound Formula VIII-1 wherein Z is CN is converted into a compound of Formula VIII-2 wherein Z is $COOR^1$. The hydrolysis can be carried out using methods known in the art, including chemical or enzymatic catalysis methods as described in Method 1.

Compounds of Formulas VIII-2 can then be cyclized to provide the N-3 benzimidazole core structure represented by Formula Ia-2 wherein Z is $COOR^1$. The cyclization step to provide the benzimidazole core structure can be performed in several ways, such as any one of Methods A, C and D as described later in detail.

Method 3: In yet another embodiment, the present invention provides a method, referred to herein as Method 3, for preparing compounds of Formula Ia-2 and their synthetic intermediates. Method 3, as illustrated in FIG. 1, follows the $S_NAr$ route of Method 1, with the exception that the CN group is converted into $COOR^1$ at an earlier stage in the synthetic route. In particular, according to Method 3, a compound of Formula VII-1a or VII-1b wherein Z is CN is converted into a compound of Formula VII-2a or VII-2, respectively, wherein Z is $COOR^1$. The conversion of the nitrile moiety of the compound of Formula VII-1a or VII-1b to a $COOR^1$ group, wherein $R^1$ is as defined herein, can be carried out using methods known in the art, including chemical or enzymatic catalysis methods as described in Method 1.

Compounds of Formulas VII-2a and VII-2b can then be converted to a compound of Formula VIII-2 upon reduction the nitro moiety using conditions such as those described in Method 1. Compounds of Formulas VIII-2 can be cyclized to provide the N-3 benzimidazole core structure represented by Formula Ia-2 wherein Z is $COOR^1$. The cyclization step to provide the benzimidazole core structure can be performed in several ways, such as any one of Methods A, C or D as described later in detail.

Method 4: In yet another embodiment, the present invention provides a process, referred to herein as Method 4, for preparing N-1 benzimidazole compounds represented by Formula Ib-2 and their synthetic intermediates

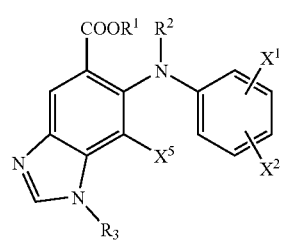

Ib-2 and salts and solvates thereof, wherein $R^1$, $R^2$, $R^3$, $X^1$, $X^2$ and $X^5$ are as defined herein, with the proviso that $R^3$ is not hydrogen. Method 4, as illustrated in FIG. 1, follows the $S_NAr$ route of Method 1 up through the preparation of a compound of Formula VIII

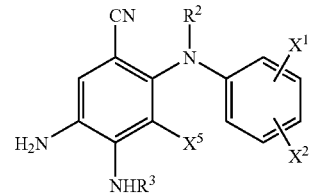

VIII-1 wherein $R^2$, $R^3$, $X^1$, $X^2$ and $X^5$ are as defined herein. Cyclization of the compound of Formula VIII-1 according to Method B described below in detail provides a 1-H benzimidazole of Formula Ib-1

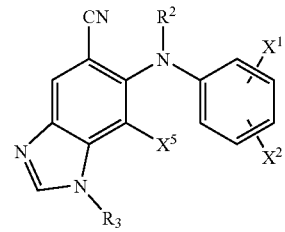

Ib-1 wherein $R^2$, $R^3$, $X^1$, $X^2$ and $X^5$ are as defined herein.

Conversion of the nitrile function in Ib-1 to a $COOR^1$ group, wherein $R^1$ is as defined herein, can then be carried out methods known in the art, including chemical or enzymatic catalysis methods as described in Method 1, to provide a compound of Formula Ib-2.

Methods 1-4 of the present invention provide a number of distinct advantages over conventional processes for preparing compounds of the general Formulas Ia-2, Ib-1 and Ib-2. For example, the processes of the present invention provide compounds of the general Formulas Ia-1, Ia-2, Ib-1 and Ib-2 in higher yields compared to conventional processes. Further, the invention provides methods for the regioselective and chemoselective cyclization of compounds of Formulas VIII-1 and to provide benzimidazoles of Formulas Ia-1, Ia-2, Ib-1 and Ib-2, respectively. In addition, the process of the present invention is more reliable and suitable for the large-scale synthesis of benzimidazoles than conventional processes. For example, the cyclization of a compound of Formula VIII-1 to a compound of Formula Ia-1, according to the Methods A and C-E described below in detail, or the cyclization of a compound of Formula VIII-1 to a compound of Formula Ib-1 according to Method B described below, produces far less toxic by-products than methods utilized in the prior art for the synthesis of benzimidazole ring systems, and is a more efficient process. The synthetic methods of the present invention are selective and the preparation of the compounds of this invention can be carried out in high yield, thus providing industrial value. Furthermore, benzimidazole derivatives represented by Formulas Ia-1, Ib-1, Ia-2 and Ib-2 can be synthesized from trihalobenzoic acids in a relatively short number of steps.

Benzimidazole Cyclizations

As stated, the cyclization of compounds of Formula VIII-1 or VIII-2 in any of Methods 1-4 of the present invention to provide benzimidazole core structures Ia-1, Ia-2, Ib-1 or Ib-2 can be performed in several ways. Five methods, namely Methods A-E, are described below and are illustrated in FIGS. 3-7. The cyclization methods provide either N-3 benzimidazole derivatives or N-1 benzimidazole derivatives, depending on the reagents employed and the nature of the $R^3$ substituent. Methods A-E are described below with respect to the cyclization of compounds of Formula VIII-1. However, it is to be understood that these cyclization methods apply equally to the cyclization of compounds of Formula VIII-2.

Figure 3:
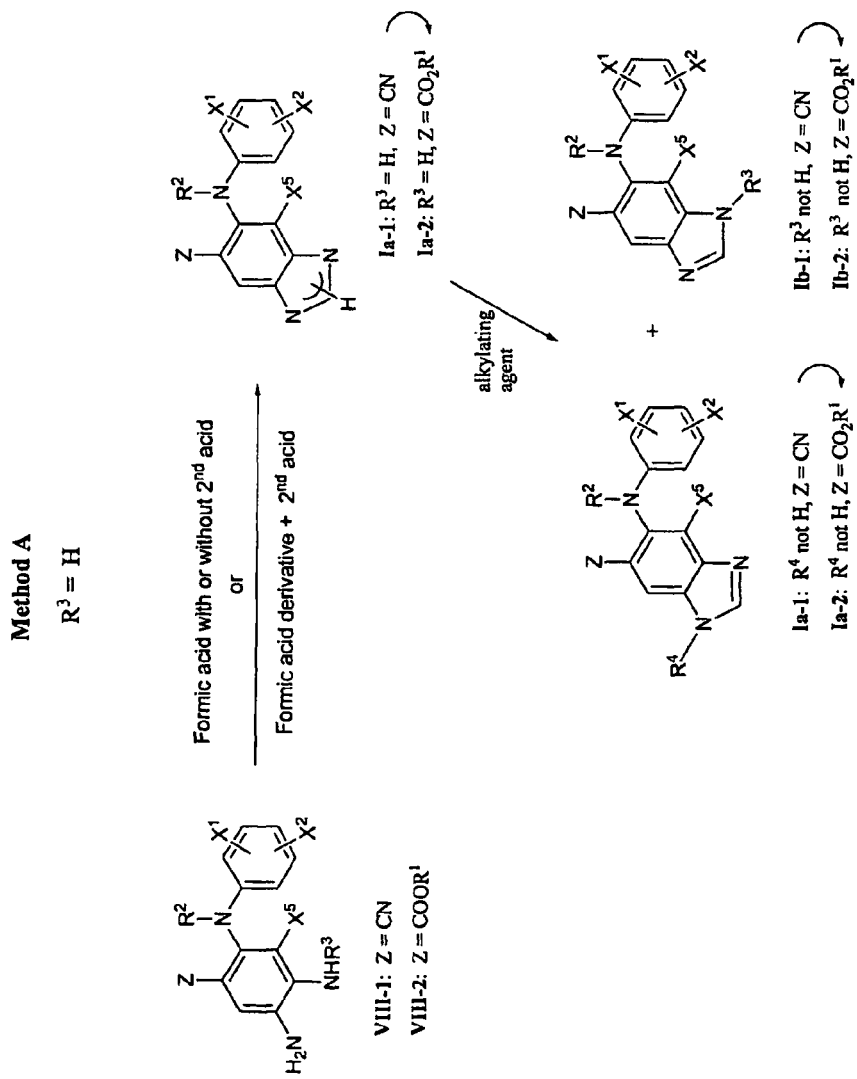
FIG. 3 shows a "one pot" cyclization method (Method A) using formic acid or a formic acid derivative for the preparation of benzimidazole tautomers represented by Formula Ia-1 wherein $R^4$ is hydrogen.

Method A: According to cyclization Method A, as shown in FIG. 3, a compound of Formula

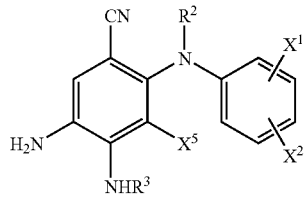

VIII-1 wherein $R^2$, $X^1$, $X^2$ and $X^5$ are as defined herein and $R^3$ is hydrogen, can be cyclized to the corresponding benzimidazole tautomer represented by Formula Ia-1

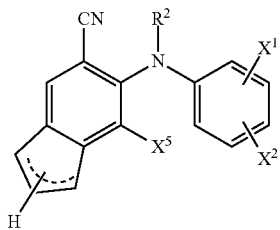

Ia-1 according to a "one-pot" process which comprises reacting a compound of Formula VIII-1 with (i) formic acid optionally in the presence of an additional acid, or (ii) a formic acid derivative in the presence of an acid, under appropriate conditions known to those skilled in the art. As used herein, the term "formic acid derivative" includes, but is not limited to, esters of formic acid such as, but not limited to, trimethylorthoformate, triethylorthoformate, and formamidine acetate. For example, in one embodiment, a compound of Formula VIII-1 wherein $R^3$ and $R^{3a}$ are hydrogen was converted into a compound of Formula Ia-2 in very high yield upon reaction with methyl orthoformate and sulfuric acid in THF solution. If desired, the compound of Formula Ia-2 can be reacted with an alkylating agent to provide a mixture of the N-1 and N-3 alkylated benzimidazoles Ia-2 and Ib-2

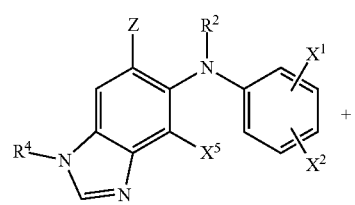

Ia-2

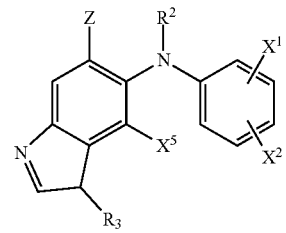

Ib-2 wherein $R^4$ and $R^3$ are not hydrogen.

Figure 4:
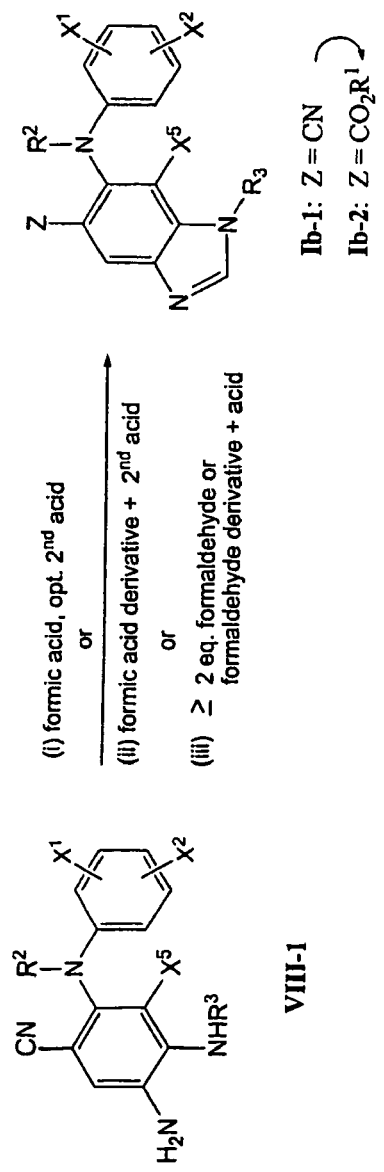
FIG. 4 shows a "one pot" cyclization method (Method B) using formic acid, a formic acid derivative, formaldehyde or a formaldehyde derivative for the preparation of benzimidazole core structures represented by Formula Ib-1 wherein $R^3$ is not hydrogen.

Method B: According to cyclization Method B, as shown in FIG. 4, a compound of Formula VIII-1, wherein $R^3$ is not hydrogen, can be cyclized to the corresponding N-1 benzimidazole derivative represented by Formula Ib-1

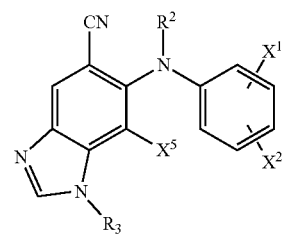

Ib-1 wherein $R^2$, $R^3$, $X^1$, $X^2$ and $X^5$ are as defined herein according to a "one-pot" process which comprises reacting a compound of Formula VIII-1 with (i) formic acid, optionally in the presence of a second acid, (ii) a formic acid derivative in the presence of an acid, or (iii) formaldehyde or a formaldehyde derivative in the presence of an acid under appropriate conditions known to those skilled in the art to provide the N-1 benzimidazole derivative represented by Formula Ib-1 wherein $R^3$ is not hydrogen.

Figure 5:
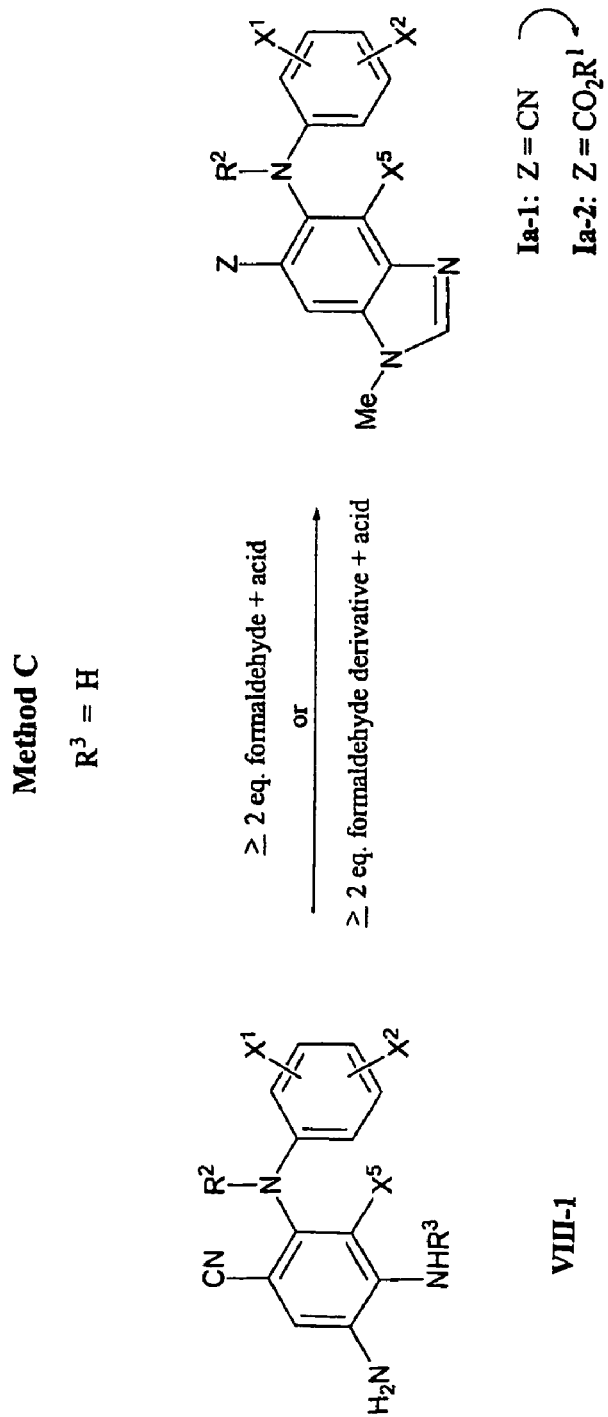
FIG. 5 shows a "one pot" cyclization method (Method C) using formaldehyde or a formaldehyde derivative for the preparation of benzimidazoles represented by Formula Ia-1 wherein $R^4$ is methyl.

Method C: Cyclization Method C, as shown in FIG. 5, provides a "one pot" method for selectively and directly converting a compound of Formula VIII-1, wherein $R^3$ is hydrogen, to an N-3 benzimidazole derivative represented by Formula Ia-1

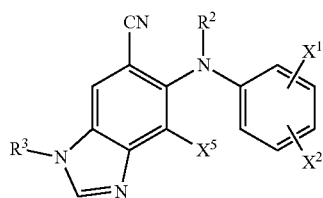

Ia-1 wherein $R^2$, $X^1$, $X^2$ and $X^5$ are as defined herein and $R^4$ is methyl. Method C comprises treating a compound of Formula VIII-1 or VIII-2 with two or more equivalents of formaldehyde or a formaldehyde derivative in the presence of an acid. This reaction advantageously proceeds with complete regioselectivity to provide N-3 methyl benzimidazoles represented by Formula Ia-1. As used herein, the term "formaldehyde derivative" includes, but is not limited to, dialkoxymethanes such as diethoxymethane and dimethoxymethane. Suitable acids for purposes of this invention include mineral acids (e.g., sulfuric acid, HCl, HBr), sulfonic acids (methanesulfonic acid, toluenesulfonic acid, etc.) and carboxylic acids (e.g., formic acid, acetic acid, etc.). In one non-limiting embodiment, the reaction is performed in acetonitrile containing water and diethoxymethane or dimethoxymethane in the presence of an acid such as toluenesulfonic acid.

Figure 6:
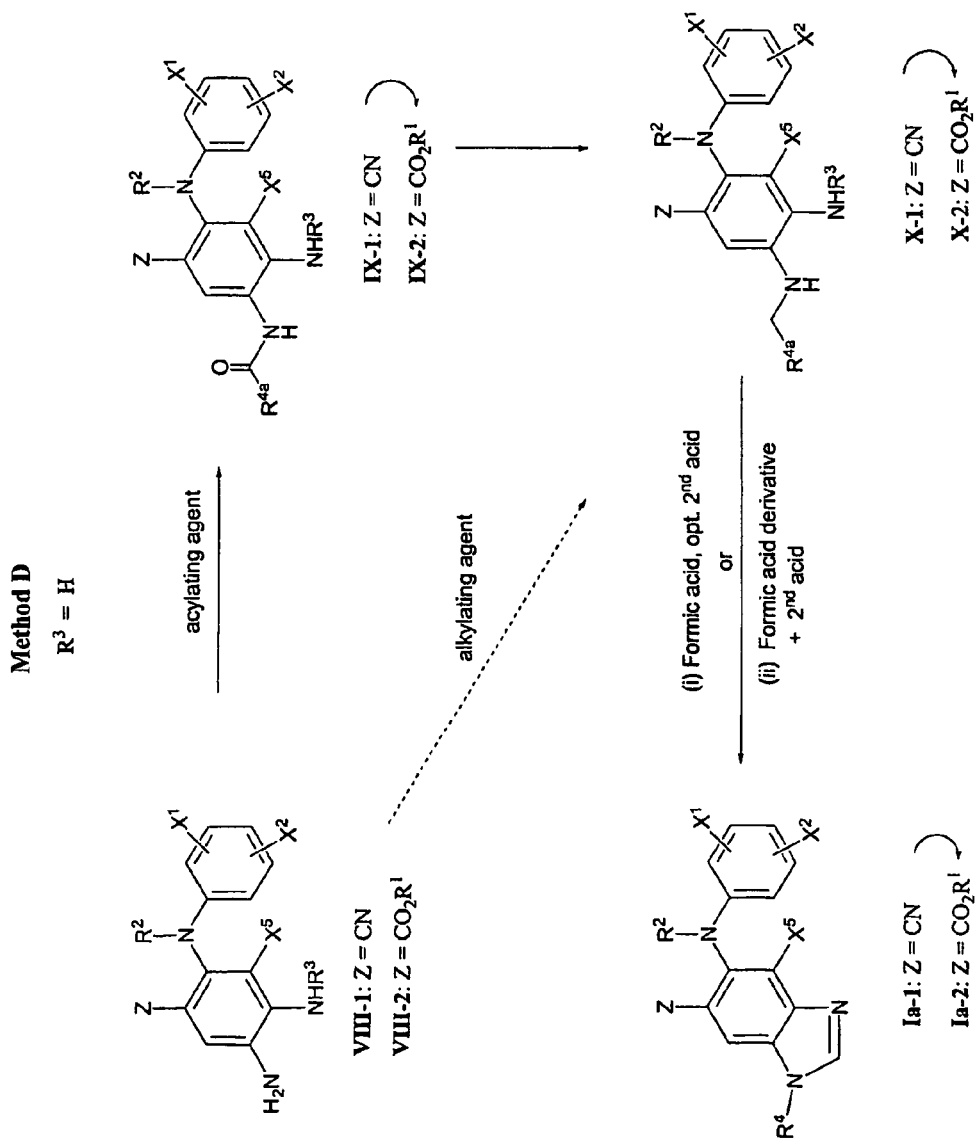
FIG. 6 shows a multi-step cyclization method (Method D) for the preparation of benzimidazoles represented by Formula Ia-1 wherein $R^4$ is not hydrogen.

Method D: According to another embodiment, an N-3 benzimidazole derivative represented by Formula Ia-1, wherein $R^4$ is not hydrogen, can be prepared from a compound of Formula VIII-1 in a stepwise manner as shown in FIG. 6. More specifically, Method D comprises treating a compound of Formula VIII-1 wherein $R^3$ is hydrogen, with a suitable acylating agent such as, but not limited to, formic acid, an acid anhydride (for example acetic anhydride), an acid halide (for example acetyl chloride) or an ester (for example trifluoroethyl formate) to provide the intermediate compound represented by Formula IX-1

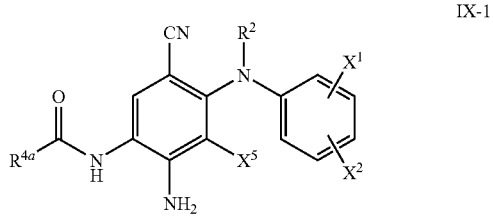

wherein $R^2$, $X^1$, $X^2$ and $X^5$ are as defined herein and $R^{4a}$ is H, $C_1$-$C_{10}$ alkyl, $C_3$-$C_{10}$ cycloalkylalkyl, arylalkyl, heteroarylalkyl or heterocyclylalkyl, wherein said alkyl, cycloalkylalkyl, arylalkyl, heteroarylalkyl, and heterocyclylalkyl portions are optionally substituted with one or more groups independently selected from halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^6R^7$ and —$OR^8$.

The amide group of the compound of Formula IX-1 is then reduced to provide an intermediate compound represented by Formula X-1

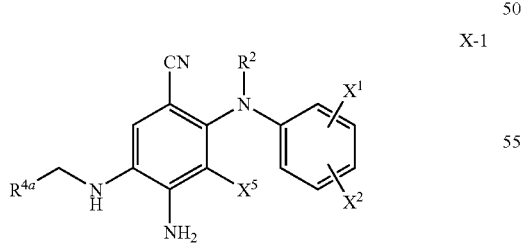

wherein $R^2$, $R^{4a}$, $X^1$, $X^2$ and $X^5$ are as defined herein. Suitable reducing agents include, but are not limited to, borane-type reducing agents (e.g., $BH_3$.THF) in an appropriate solvent such as THF.

Alternatively, a compound of Formula X-1 can be formed directly from a compound of Formula VIII-1 as shown in FIG. 6 by reaction with an alkylating agent. Examples of suitable alkylating agents include, but are not limited to, alkyl halides (such as ethyl iodide), alkyl tosylates, alkyl mesylates and alkyl triflates.

Cyclization of the compound of Formula X-1 to provide the benzimidazole represented by Formula Ia-1

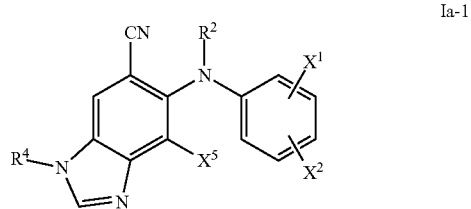

wherein $R^4$ is not hydrogen, is accomplished by reacting the compound of Formula X-1 with (i) formic acid optionally in the presence of a second acid or (ii) a formic acid derivative in the presence of an acid, under appropriate conditions known to those skilled in the art to provide a compound of Formula Ia-1. Examples of suitable formic acid esters include, but are not limited to, trimethylorthoformate, triethylorthoformate and formamidine acetate.

Figure 7:
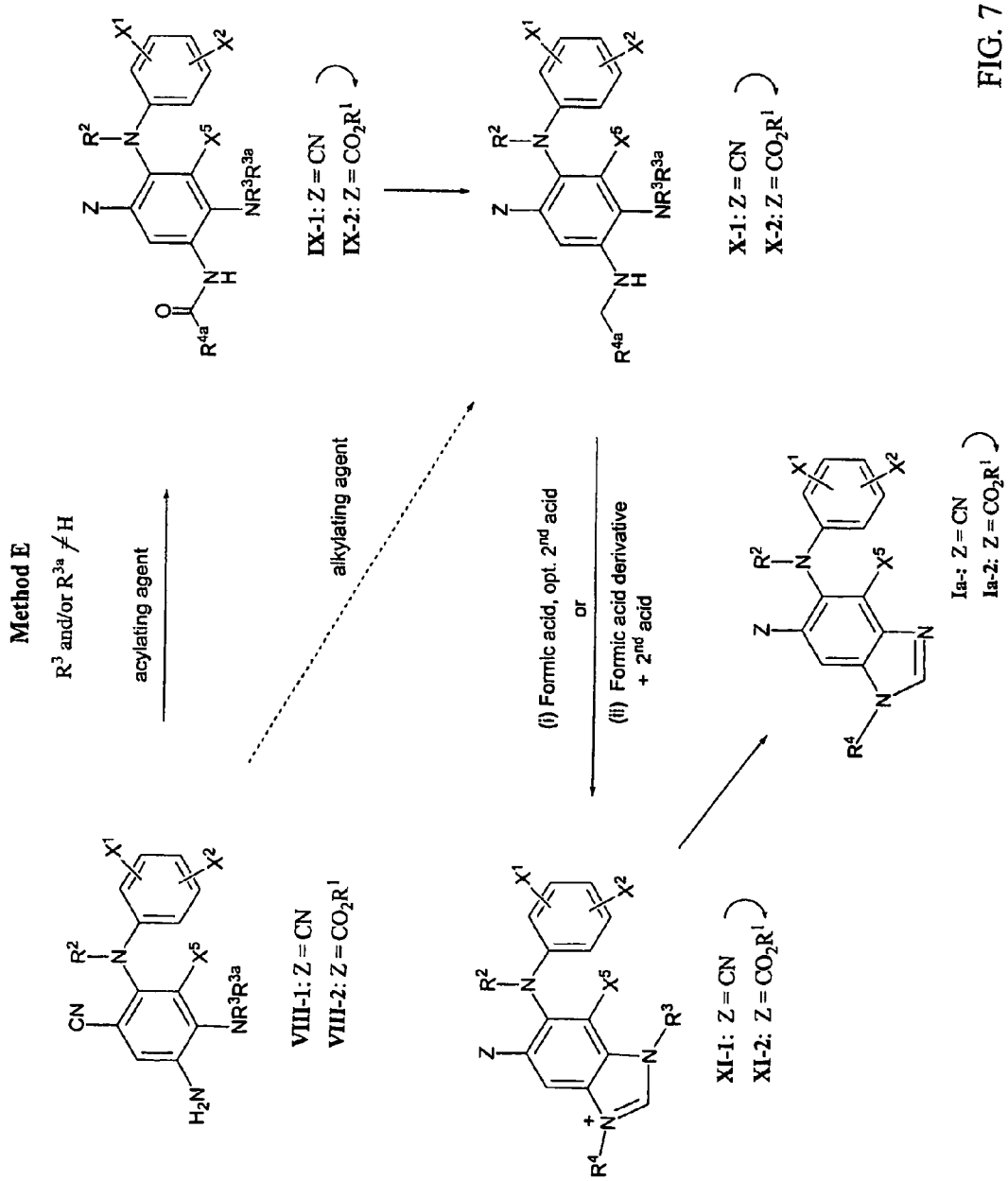
FIG. 7 shows another multi-step cyclization method (Method E) for the preparation of benzimidazoles represented by Formula Ia-1 wherein $R^4$ is not hydrogen.

Method E: In an alternative multi-step cyclization method, referred to herein as Method E, an N-3 benzimidazole derivative represented by Formula Ia-1, wherein $R^4$ is not hydrogen, can be prepared from a compound of Formula VIII-1 in a stepwise manner as shown in Figure as shown in FIG. 7.

More specifically, Method E comprises treating a compound of Formula VIII-1, wherein $R^3$ is not hydrogen, with a suitable acylating agent such as, but not limited to, formic acid, an acid anhydride (for example acetic anhydride), an acid halide (for example acetyl chloride) or an ester (for example trifluoroethyl formate) to provide the intermediate compound represented by Formula IX-1

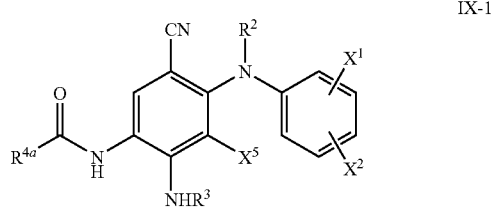

wherein $R^2$, $R^3$, $X^1$, $X^2$ and $X^5$ are as defined herein and $R^{4a}$ is H, $C_1$-$C_{10}$ alkyl, $C_3$-$C_{10}$ cycloalkylalkyl, arylalkyl, heteroarylalkyl or heterocyclylalkyl, wherein said alkyl, cycloalkylalkyl, arylalkyl, heteroarylalkyl, and heterocyclylalkyl portions are optionally substituted with one or more groups independently selected from halogen, hydroxyl, cyano, nitro, azido, $C_1$-$C_4$ alkyl, $C_2$-$C_4$ alkenyl, $C_2$-$C_a$ alkynyl, $C_3$-$C_6$ cycloalkyl, $C_3$-$C_6$ heterocycloalkyl, —$NR^6R^7$ and —$OR^8$.

The amide group of the compound of Formula IX-1 is then reduced to provide an intermediate compound represented by Formula X-1

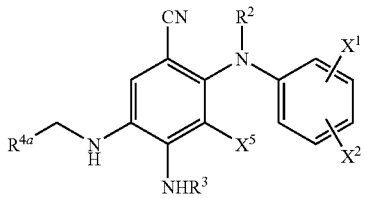

wherein $R^2$, $R^3$, $R^{4a}$, $X^1$, $X^2$ and $X^5$ are as defined herein. Suitable reducing agents include, but are not limited to, borane-type reducing agents (e.g., $BH_3.THF$) in an appropriate solvent such as THF. Alternatively, a compound of Formula X-1 can be formed directly from a compound of Formula VIII-1 as shown in FIG. 7 by reaction with an alkylating agent as discussed in Method D. Cyclization of the compound of Formula X-1 to provide the benzimidazole represented by Formula XI-1

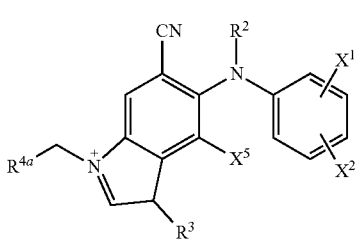

wherein $R^2$, $R^3$, $R^{4a}$, $X^1$, $X^2$ and $X^5$ are as defined herein. Removal of the $R^3$ group from said compound of Formula XI-1 provides the N-3 benzimidazole compound of Formula Ia-1.

Methods for removing N-1 substituents from benzimidazoles are well known to persons skilled in the art, and the reagents and reaction conditions required depend on the nature of the $R^3$ group. For example, when the $R^3$ group of a compound of Formula XI-1 is N-alkyl, N-allyl, N-benzyl, —C(O)OR$^5$ or —COR$^5$, removal of the $R^3$ group can be achieved by hydrogenation. An N-1 allyl substituent can also be removed from a compound of Formula XI-1 by heating the compound of Formula XI-1 in the presence of an organometallic catalyst such as $Rh(PPh_3)_3Cl$, also known as Wilkinson's catalyst.

Examples of formic acid esters for the cyclization Methods A, B, C and E include trimethylorthoformate, triethylorthoformate, and formamidine acetate.

The above-described cyclization Methods A-E of the present invention offer several advantages over conventional methods for the preparation of benzimidazole derivatives. First, there are only a few literature examples of the conversion of a diamino aryl compound to a benzimidazole (see, for example, G. P. Ellis, R. T. Jones, *J. Chem. Soc., Perkin 1*, 1974, 903; G. T. Morgan, W. A. P. Challenor, *J. Chem. Soc. Trans.*, 1921, 1537; N. S. Zefirov, et al., *Zyk, ECHET98: Electronic Conference on Heterocyclic Chemistry*, (1988) 406-408; V. Milata, D. Ilaysky, *Organic Proc. And Prep. Int.*, (1993), 25:703-704), however, none of the reported examples involved highly substituted substrates such as those involved in the process of the present invention. In addition, in many of the literature examples the regioselectivity is uncertain (G. T. Morgan, W. A. P. Challenor, *J. Chem. Soc. Trans.*, 1921, 1537). Furthermore, the methods of this invention are more suitable for industrial applications, since it uses reagents that are less toxic than the HCl/HCHO reagent mixture used in conventional methods, and therefore do not generate toxic by-products such as dichloromethyl ether.

The terms "$C_1$-$C_{10}$ alkyl" and "alkyl" as used herein refer to a saturated linear or branched-chain monovalent hydrocarbon radical having one to ten carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, neopentyl, tert-pentyl, hexyl, 2-hexyl, 3-hexyl, 3-methylpentyl, heptyl, octyl, and the like.

The terms "$C_2$-$C_{10}$ alkenyl" and "lower alkenyl" refer to linear or branched-chain monovalent hydrocarbon radical having two to 10 carbon atoms and at least one double bond, and include, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations.

The terms "$C_2$-$C_{10}$ alkynyl" and "alkynyl" refer to a linear or branched monovalent hydrocarbon radical of two to twelve carbon atoms containing at least one triple bond. Examples include, but are not limited to, ethynyl, propynyl, butynyl, pentyn-2-yl and the like, wherein the allynyl radical may be optionally substituted independently with one or more substituents described herein.

The terms "carbocycle," "carbocyclyl," "cycloalkyl" or "$C_3$-$C_{10}$ cycloalkyl" refer to saturated or partially unsaturated cyclic hydrocarbon radical having from three to ten carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. The cycloalkyl may be optionally substituted independently in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$) alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" or "heterocyclyl" refer to a saturated or partially unsaturated carbocyclic radical of 3 to 8 ring atoms in which at least one ring atom is a heteroatom selected from nitrogen, oxygen and sulfur, the remaining ring atoms being C, wherein one or more ring atoms may be optionally substituted independently with one or more substituent described below. The radical may be a carbon radical or heteroatom radical. The term further includes bicyclic and tricyclic fused ring systems, which include a heterocycle fused one or more carbocyclic or heterocyclic rings. "Heterocycloalkyl" also includes radicals wherein heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$) alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$) alkyl, mono($C_1$-$C_6$)alkylamino($C_1$-$C_6$)alkyl or di($C_1$-$C_6$) alkylamino($C_1$-$C_6$)alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halogen, lower alkyl, lower alkoxy, trifluoromethyl, aryl, heteroaryl, and hydroxy.

The term "heteroaryl" refers to a monovalent aromatic radical of 5-, 6- or 7-membered rings which includes fused ring systems (at least one of which is aromatic) of 5-10 atoms containing at least one and up to four heteroatoms selected from nitrogen, oxygen, or sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally mono-, di-, or trisubstituted with, e.g., halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, and $C_3$-$C_6$ heterocycloalkyl.

The term "arylalkyl" means an alkyl moiety (as defined above) substituted with one or more aryl moiety (also as defined above). More preferred arylalkyl radicals are aryl-$C_{1-3}$-alkyls. Examples include benzyl, phenylethyl, and the like.

The term "heteroarylalkyl" means an alkyl moiety (as defined above) substituted with a heteroaryl moiety (also as defined above). More preferred heteroarylalkyl radicals are 5- or 6-membered heteroaryl-$C_{1-3}$-alkyls. Examples include oxazolylmethyl, pyridylethyl and the like.

The term "heterocyclylalkyl" means an alkyl moiety (as defined above) substituted with a heterocyclyl moiety (also defined above). More preferred heterocyclylalkyl radicals are 5- or 6-membered heterocyclyl-$C_{1-3}$-alkyls. Examples include tetrahydropyranylmethyl.

The term "cycloalkylalkyl" means an alkyl moiety (as defined above) substituted with a cycloalkyl moiety (also defined above). More preferred heterocyclyl radicals are 5- or 6-membered cycloalkyl-$C_{1-3}$-alkyls. Examples include cyclopropylmethyl.

The term "Me" means methyl, "Et" means ethyl, "Bu" means butyl and "Ac" means acetyl.

The term "halogen" represents fluorine, bromine, chlorine, and iodine.

In general, the various moieties or functional groups of any of the compounds of the present invention may be optionally substituted by one or more substituents. Examples of substituents suitable for purposes of this invention include, but are not limited to, oxo (with the proviso that it is not on an aryl or heteroaryl), halogen, cyano, nitro, trifluoromethyl, difluoromethoxy, trifluoromethoxy, azido, —OR', —NR'SO$_2$R"", —SO$_2$NR'R", —C(O)R', —C(O)OR', —OC(O)R', —NR'C (O)OR"", —NR'C(O)R", —C(O)NR'R", —SR', —S(O)R"", —SO$_2$R"", —NR'R", —NR'C(O)NR"R"', —NR'C(NCN) NR"R"', aryl, heteroaryl, arylalkyl, heteroarylalkyl, heterocyclyl and heterocyclylalkyl, where R', R", R"' and R"" are independently lower alkyl, lower alkenyl, or lower alkynyl.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

Certain compounds prepared according to a process of the present invention can exist as two or more tautomeric forms. Tautomeric forms of the compounds may interchange, for example, via enolization/de-enolization and the like. Accordingly, the present invention includes the preparation of all tautomeric forms of compounds of Formulas Ia-1, Ia-2 Ib-1 and Ib-2 wherein $R^4$ is hydrogen.

This invention also encompasses compounds of Formulas VIII-1, VIII-2, XI-1, Ia-1, Ia-2 Ib-1 and Ib-2.

This invention further includes solvates of compound of Formula VIII-1, VIII-2, XI-1, Ia-1, Ia-2 Ib-1 and Ib-2. The term "solvate" refers to an aggregate of a compound of this invention with one or more solvent molecules.

This invention also encompasses salts of compounds of Formula VIII-1, VIII-2, XI-1, Ia-1, Ia-2 Ib-1 and Ib-2. That is, a compound of the invention may possess a sufficiently acidic, a sufficiently basic, or both functional groups, and accordingly react with any of a number of inorganic or organic bases, and inorganic and organic acids, to form a salt. Examples of salts include those salts prepared by reaction of the compounds of the present invention with a mineral or organic acid or an inorganic base, such salts including sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the inventive compound is a base, the desired salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

The inventive compounds may be prepared using the reaction routes and synthesis schemes as described herein, employing the techniques available in the art using starting materials that are readily available or can be synthesized using methods known in the art.

Representative compounds of the present invention, which are encompassed by the present invention include, but are not limited to, the compounds of the examples and the acid or base addition salts thereof. The examples presented below are intended to illustrate particular embodiments of the invention, and are not intended to limit the scope of the specification or the claims in any way.

EXAMPLES

The example and preparations provided below further illustrate and exemplify the compounds of the present invention and methods of preparing such compounds. It is to be understood that the scope of the present invention is not limited in any way by the scope of the following examples and preparations. Persons skilled in the art will recognize that the chemical reactions described may be readily adapted to prepare a number of other MEK inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the example described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane, toluene, dioxane and 1,2-difluoroethane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

$^1$H-NMR spectra were recorded on a Varian or Buker instrument operating at 400 or 500 MHz. $^1$H-NMR spectra were obtained as $CDCl_3$ or DMSO-$d_6$ solutions (reported in ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

Preparation of 6-(4-bromo-2-chlorophenylamino)-7-fluoro-3-methyl-3H-benzoimidazole-5-carboxylic acid

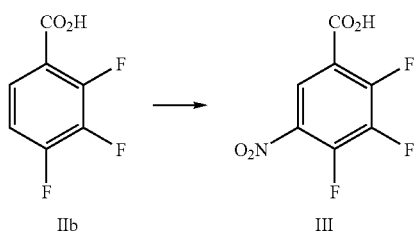

Step A: 2,3,4-Trifluoro-5-nitrobenzoic acid; Fuming $HNO_3$ 90% (549.0 g, 7.84 mol corrected for 90% wt, 1.26 equiv.) was added to 2.0 L (3.35 kg) of concentrated $H_2SO_4$ over 18 minutes with stirring. The solution of $HNO_3$ was then added to a mixture of 2,3,4-trifluorobenzoic acid (1094 g, 6.21 mol, 1 equiv.) in 3.3 L (5.85 kg) of concentrated $H_2SO_4$ in a second flask with ice-water bath cooling over an hour. When addition was complete, the reaction solution was allowed to warm to room temperature. After 5 hours, the reaction was complete as determined by HPLC and the reaction mixture (brown solution) was poured into a mechanically stirred mixture of 10.6 kg of distilled water and 11.8 kg of ice over 10 minutes. The yellow slurry was cooled to 14° C., stirred for 2 hours and then filtered. The cake was rinsed with 4.0 L of distilled water and then with 5 L of heptane. The wet cake was oven-dried overnight. The crude solids (1.791 kg) were then stirred in 16 L of distilled water (9 vol.), filtered and oven-dried at 55° C. under high vacuum overnight to yield 1035.9 g (75%) of 2,3,4-trifluoro-5-nitrobenzoic acid as a yellowish solid. HPLC was 98a % (220 nm) and 100% (254 nm). $^1$H NMR. (400 MHz, DMSO-$d_6$) δ 8.44 (1H, apparent dt, J 1.9, 7, Ar—H); $^{19}$F NMR (376 MHz, DMSO-$d_6$) δ −153.9, −131.5, −120.9. $^{13}$C NMR (100 MHz, DMSO-$d_6$) δ 117 (C, m), 124 (CH, b s), 134 (C, s), 141 (C—F, dt, J 251, 10), 148 (C—F, dd, J 265, 13), 154 (C—F, dd, J 265, 10), 163 (COOH). IR $v_{max}$/cm$^{-1}$ 3108 (br), 1712, 1555, 1345, 1082. MS APCI (−) m/z 220 (M−1) detected.

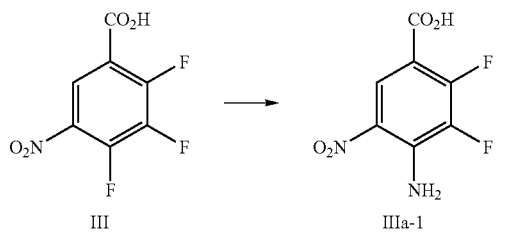

Step B: 4-Amino-2,3-difluoro-5-nitrobenzoic acid: To a mixture of 2,3,4-trifluoro-5-nitrobenzoic acid (167.2 g, 0.756 mol, 1 equiv.) in 400 mL of distilled water was added concentrated ammonium hydroxide (28% $NH_3$ solution; 340 g, 380 mL, 4.23 mol, 5.6 equiv), ensuring that internal temperature was below 6.0° C. over 2-2.5 hours. The mixture was stirred for 50 minutes and then warmed to room temperature for 3-4 hours. When the reaction was >90% complete as determined by HPLC, the mixture was cooled in an ice-water bath, and concentrated HCl (350 mL) was then added dropwise to adjust pH=2. The slurry was stirred for 1 hour with ice bath cooling and then filtered. The cake was rinsed with 1 L of distilled water and then with 350 mL of MTBE. The cake was oven-dried at 48° C. overnight to give 134.9 g of a yellow solid. HPLC was 83.6a % (220 nm) and 96.96 a % (254 nm). The MTBE filtrate was concentrated on a rotary evaporator and pumped overnight to give 9.9 g of a second crop as a yellow solid: HPLC was 81.1a % (220 nm) and 95.40a % (254 nm). Combined yield of 4-amino-2,3-difluoro-5-nitrobenzoic acid was 144.8 g (88%). $^1$H NMR (400 MHz, DMSO-$d_6$) δ 8.0 (2H, br s, $NH_2$) 8.42 (1H, dd, J 1.5, 7.6, Ar—H); $^{19}$F NMR (376 MHz, DMSO-$d_6$) δ −153.9, −129.0. $^{13}$C NMR (100 MHz, DMSO-$d_6$) δ 106 (C; d, J 10), 126 (CH), 128 (C), 140 (C—F, dd, J 241, 16), 140.8 (C, dd, J 12, 4), 153 (C—F, dd, J 263, 11), 164 (COOH). IR $v_{max}$/cm$^{-1}$ 3494, 3383, 1697, 1641, 1280. MS APCI (−) m/z 217 (M−1) detected.

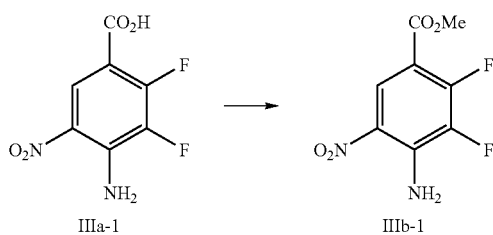

Step C: 4-Amino-2,3-difluoro-5-nitrobenzoic acid methyl ester: TMSCl (132 g, 1.21 mol, 2.0 equiv) was added over 5 minutes to a slurry of 4-amino-2,3-difluoro-5-nitrobenzoic acid (132.3 g, 0.607 mol, 1 equiv.) in 325 mL of MeOH. The mixture was heated at reflux for 15 hours. When the reaction was complete as determined by HPLC, the mixture was cooled in an ice-water bath for 45 minutes. The reaction mixture was then filtered and the cake was washed with 65 mL of MeOH. The wet cake was dried overnight at 55° C. under high vacuum to give 128.8 g (92%) of 4-amino-2,3-difluoro-5-nitrobenzoic acid methyl ester. HPLC was 97.9a % (220 nm) and 99.2a % (254 nm). $^1$H NMR (400 MHz, DMSO-$d_6$) δ 3.84 (3H, s, OMe), 8.1 (2H, br s, $NH_2$), 8.43 (1H, apparent dd, J 1.9, 7.2, Ar—H). $^{19}$F NMR (376 MHz, D6 DMSO) δ −153.6, −129.2. $^{13}$C NMR (100 MHz, DMSO-$d_6$) δ 52 ($CH_3O$), 105 (C, d, J 10), 125 (CH, t, J 2.7), 128 (CH, d, J 5), 140 (C—F, dd, J 244, 15), 141 (C, dd, J 14, 5), 152 (C—F, dd, J 263, 11), 162 (COO, t, J 3). IR $v_{max}$/cm$^{-1}$ 3433, 3322, 1699, 1637, 1548, 1342, 1234. MS APCI (−) m/z 231 (M−1) detected.

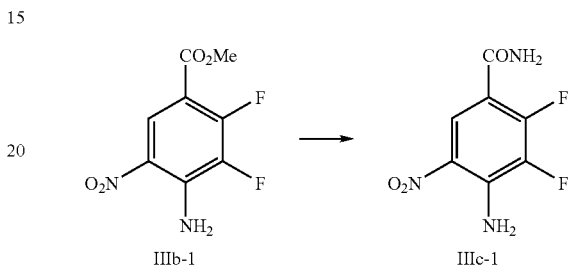

Step D: 4-Amino-2,3-difluoro-5-nitrobenzamide: A mixture of 4-amino-2,3-difluoro-5-nitrobenzoic acid methyl ester (150 g, 0.646 mol) in 14 M $NH_4OH$ (1 L, 14 mol, ~7 vol) was stirred at room temperature. After 8 days HPLC analysis showed the reaction was almost complete. The solid product was filtered off, washed with water (2×200 mL), and then dried at 50° C. in a vacuum oven to provide 4-amino-2,3-difluoro-5-nitrobenzamide (118.7 g, 85% yield) as a yellow powder. HPLC 93.3a %. $^1$H NMR (400 MHz, DMSO-$d_6$) δ 7.65 (2H, br s, $NH_2$), 7.83 (2H, br s, $NH_2$), 8.30 (1H, apparent dd, J 1.5, 7.2, Ar—H). $^{19}$F NMR (376 MHz, DMSO-$d_6$) δ −130, −154. $^{13}$C (100 MHz, DMSO-$d_6$) δ 110.7 (C, d, J 12), 123.8 (CH, s), 128.1 (C, s), 139.5 (C, dd, J 14, 4), 139.6 (CF, dd, J 243, 17), 151.7 (CF, dd, J 257, 11), 163.4 (C, s). IR $v_{max}$/cm$^{-1}$ 3496, 3419, 3385, 3179, 1653, 1279, 1240. MS APCI (−) 216 (M−1) detected.

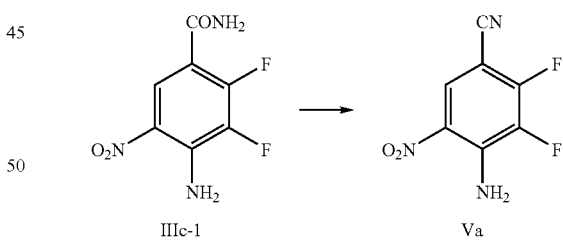

Step E: 4-Amino-2,3-difluoro-5-nitrobenzonitrile: To a stirred suspension of 4-amino-2,3-difluoro-5-nitrobenzamide (90 g, 0.416 mol) in acetonitrile (630 mL) was added $POCl_3$ (96 mL, 1.04 mol) in one portion. The mixture was then heated to 70° C. and as the reaction proceeded the suspension become a brown solution. After 1.5 hours, HPLC analysis showed no remaining starting material. The reaction mixture was cooled to 30° C., then added to water (4.5 L) over 30 minutes while the temperature was held at 17-25° C. The resultant bright yellow slurry was stirred for 1 hour, filtered under vacuum, and the remaining solid was then dried in a vacuum oven at 50° C. to provide 4-amino-2,3-difluoro-5-nitrobenzonitrile as a yellow solid, (74.4 g, 90% yield). HPLC 95a %. $^1$H NMR (400 MHz, DMSO-d$_6$) δ 8.30 (2H, br s, NH$_2$), 8.53 (1H, apparent dd, J 1.8, 6.4, Ar—H). $^{19}$F NMR (376 MHz, DMSO-d$_6$) δ −128, −152. $^{13}$C (100 MHz, DMSO-d$_6$) δ 87.1 (C, d, J 15), 113.6 (C, d, J 4), 128.6 (CH, s), 128.8 (C, d, J 5), 139.3 (CF, dd, J 245, 14), 141.5 (C, dd, J 13, 5), 152.8 (CF, dd, J 259, 12). IR ν$_{max}$/cm$^{-1}$ 3446, 3322, 2235, 1647, 1551, 1287, 1275. MS APCI (−) 198 (M−1) detected, APCI (+) 200 (M+1) detected.

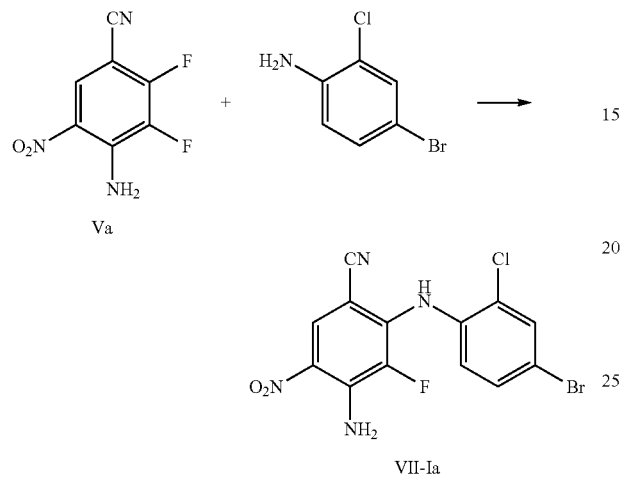

Step F: 4-Amino-2-(4-bromo-2-chlorophenylamino)-3-fluoro-5-nitrobenzonitrile: To a stirred solution of KtOBu (321 mL, 1M in THF, 0.321 mol), under nitrogen, at 10° C., was added 4 bromo-2-chloroaniline (22.8 g, 0.11 mol). The mixture quickly turned dark purple and was allowed to stir at 7-10° C. for 10 minutes before adding 4-amino-2,3-difluoro-5-nitrobenzonitrile (20 g, 0.10 mol) in THF (150 mL) over 10 minutes. After the addition was complete the mixture was allowed to warm to ambient and then stirred overnight. HPLC analysis indicated that 8% of starting material remained. Additional KtOBu (20 mL, 0.2 equiv., of 1M in THF) and 4 bromo-2-chloroaniline (1 g, 0.005 mol) were added, but after an additional 4 hours starting material still remained. The mixture was then cooled to 10° C. and treated with 2N HCl (aq) (140 mL) in one portion (temperature rose to 30° C.), then methanol (140 mL). Further amounts of water (150 mL) and methanol (200 mL) were then added and the mixture was concentrated to a thick slurry. Methanol (300 mL) was then added, the mixture was concentrated again and the solids were then filtered through a coarse fritted funnel and washed with methanol (200 mL). Once the solids started to dry they were washed with water (200 mL) and again with methanol (100 mL), then dried in the vacuum oven overnight at 50° C., to provide 25 g of 4-amino-2-(4-bromo-2-chlorophenylamino)-3-fluoro-5-nitrobenzonitrile as a light tan solid (assay ~93% by HPLC). $^1$H NMR (400 MHz, DMSO-d$_6$) δ 7.17 (1H, d, J 8.6, Ar—H), 7.50 (1H, dd, J 8.6, 2.0, Ar—H), 7.76 (1H, d, J 2, Ar—H), 7.79 (2H, br s, NH$_2$), 8.26 (1H, s, Ar—H), 8.85 (1H, br s, NH). $^{19}$F NMR (376 MHz, DMSO-d$_6$) δ −144. $^{13}$C (100 MHz, DMSO-d$_6$) δ 89.5 (C, d, J 4), 116.3 (C, d, J 4), 117.6 (CH, s), 126.7 (C, d, J 5), 127.3 (CH, s), 129.6 (C, s), 130.1 (C, d, J 2), 131.4 (CH, s), 132.4 (CH, s), 137.4 (C, d, J 11), 137.9 (C, s), 139.5 (C, d, J 5), 140.9 (CF, d, J 256). IR ν$_{max}$/cm$^{-1}$ 3448, 3338, 2360, 2342, 2217, 1640, 1539, 1313. MS APCI (−) 385 (M−1) detected.

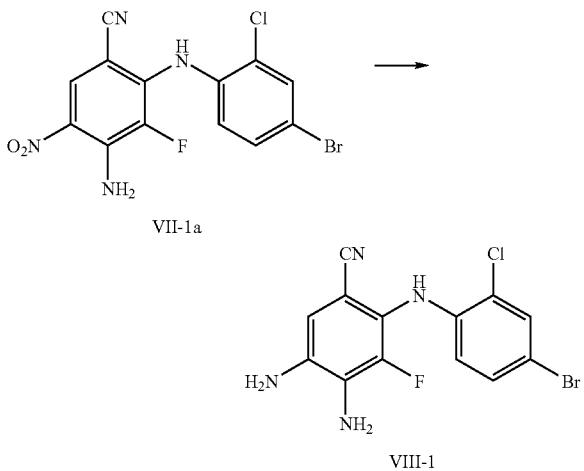

Step G: 4,5-Diamino-2-(4-bromo-2-chlorophenylamino)-3-fluorobenzonitrile:

Method 1: To a stirred solution of 4-amino-2-(4-bromo-2-chlorophenylamino)-3-fluoro-5-nitrobenzonitrile (20.0 g, 51.9 mmol) in THF (200 mL) and methanol (100 mL) was added 10 micron zinc dust (16 g, 244 mmol, 4.7 equiv). Hydrochloric acid (35 mL, 12 M, 424 mmol, 8.2 equiv.) was then added to the reaction mixture at a rate maintaining an internal temperature of ~50° C., at which time HPLC analysis indicated that no starting material remained. The mixture was allowed to cool to room temperature over 1 hour and then filtered through a coarse fritted funnel to remove any unreacted zinc. To the filtrate was added water (200 mL) followed by NH$_4$OAc (60 mL, aqueous saturated solution). The pH of the mixture was then 6-7 and most of the organic solvents were removed by evaporation under reduced pressure to provide a brown/purple suspension. The suspension was filtered to give a purple solid that was washed with water (4×50 mL). The solid was then dried in the vacuum oven, at 50° C. overnight to provide 16.0 g of 4,5-diamino-2-(4-bromo-2-chlorophenylamino)-3-fluorobenzonitrile (86% yield, >95% by HPLC). $^1$H NMR (400 MHz, DMSO-d$_6$) δ 5.22 (2H, br s, NH$_2$), 5.52 (2H, br s, NH$_2$), 6.24 (1H, d, J 8.7, Ar—H), 6.69 (1H, br s, Ar—H), 7.23 (1H, dd, J 8.6, 2, Ar—H), 7.44 (1H, s, NH), 7.54 (1H, d, J 2.1, Ar—H). $^{19}$F NMR (376 MHz, DMSO-d$_6$) δ −141. $^{13}$C (100 MHz, DMSO-d$_6$) δ 98.1 (C, d, J 4), 108.8 (CH, s), 112.5 (C, s), 115.4 (C, s), 118.8 (C, d, J 4), 119.7 (CH, s), 121.4 (C, d, J 14), 129.7 (C, d, J 15), 131.3 (s, CH), 131.9 (CH, s), 135.8 (C, d, J 8), 143.4 (C, s), 146.8 (CF, d, J 235). IR ν$_{max}$/cm$^{-1}$ 3380, 2203, 1634, 1594, 1519, 1506. MS APCI (−) 355 (M−1) detected.

Method 2: A stirred mixture of 4-amino-2-(4-bromo-2-chlorophenylamino)-3-fluoro-5-nitrobenzonitrile (200 mg, 0.52 mmol) and 5% Pt/C (40 mg) in THF (4 mL) and methanol (2 mL) was hydrogenated under 1 atm. of hydrogen overnight. The mixture was then filtered through a syringe filter and the solvents were removed under reduced pressure to provide a tan solid residue, which was further dried under high vacuum for 2 hours to provide 171 mg of 4,5-diamino-2-(4-bromo-2-chlorophenylamino)-3-fluorobenzonitrile (84% yield, at ~90% assay by HPLC [~0.18% des-bromo derivative by HPLC]). $^1$H NMR (400 MHz, DMSO-d$_6$) δ 5.22 (2H, br s, NH$_2$), 5.52 (2H, br s, NH$_2$), 6.24 (1H, d, J 8.7, Ar—H), 6.69 (1H, br s, Ar—H), 7.23 (1H, dd, J 8.6, 2, Ar—H), 7.44 (1H, s, NH), 7.54 (1H, d, J 2.1, Ar—H). $^{19}$F NMR (376 MHz, DMSO-d$_6$) δ −141.

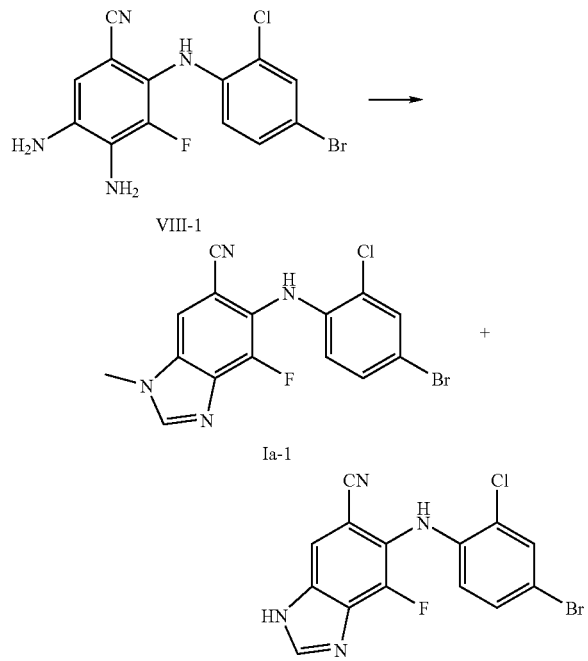

Step H: 6-(4-Bromo-2-chlorophenylamino)-7-fluoro-3-methyl-3H-benzoimidazole-5-carbonitrile: To a stirred solution of 4,5-diamino-2-(4-bromo-2-chlorophenylamino)-3-fluorobenzonitrile (5 g, 14 mmol) and diethoxymethane (2.6 mL, 29.5 mmol) in THF (50 mL) at room temperature was added concentrated sulfuric acid (1.5 mL, 28 mL, 14.1 mmol) over 5 minutes. The reaction mixture was then heated to 50° C. for 4 hours, after which HPLC analysis indicated that 6% starting material remained. A further aliquot of diethoxymethane (0.5 mL, 0.2 equiv.) was added and heating at 50° C. was continued for an additional 1.5 hours, when HPLC indicated that no starting material remained. The mixture was allowed to cool to room temperature and treated first with water (30 mL) (pH was 1), then slowly with aqueous sodium hydroxide solution (about 6 mL, 5N) and more water (20 mL) until the pH was 6-7. Isopropanol (70 mL) was then added and most of the THF was removed on a rotary evaporator until the mixture became a thick purple slurry, which was then filtered through a medium flitted funnel. The purple solid residue was washed with 50% iPrOH/water (2×20 mL), then dried in a vacuum oven at 50° C. overnight to provide 3.7 g of 6-(4-bromo-2-chlorophenylamino)-7-fluoro-3-methyl-3H-benzoimidazole-5-carbonitrile (69.3% yield). HPLC analysis indicated that the material had an assay of 86%. $^1$H NMR (400 MHz, DMSO-d$_6$) δ 3.93 (3H, s, CH$_3$), 6.26 (1H, d, J 8.6, Ar—H), 7.23 (1H, d, J 8.8, Ar—H), 7.61 (1H, d, J 2.1, Ar—H), 7.89 (s, Ar—H), 8.23 (s, Ar—H), 8.53 (s, NH). $^{19}$F NMR (376 MHz, DMSO-d$_6$) 6-134. $^{13}$C (100 MHz, DMSO-d$_6$) δ 32.1 (Me, s), 107.4 (C, d, J 2), 109.6 (CH, s), 114.0 (C, d, J 4), 115.6 (C, s), 117.7 (C, d, J 4), 120.2 (CH, s), 123.6 (C, d, J 12), 131.4 (CH, s), 132.1 (CH, s), 136.0 (C, d, J 9), 136.4 (C, d, J 15), 143 (C, s), 149.6 (CH, s), 150.2 (CF, d, J 250). IR ν$_{max}$/cm$^{-1}$ 2360, 2342, 1507. MS APCI (−) 379 (M−1) detected.

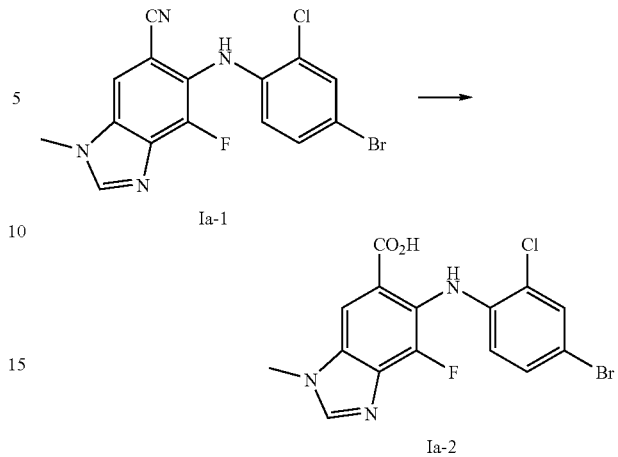

Step I: 6-(4-Bromo-2-chlorophenylamino)-7-fluoro-3-methyl-3H-benzoimidazole-5-carboxylic acid: To a stirred mixture of 6-(4-bromo-2-chlorophenylamino)-7-fluoro-3-methyl-3H-benzoimidazole-5-carbonitrile (200 mg, 0.53 mmol) in ethanol/water/THF (ratio 2:1:0.3) was added solid KOH (0.15 g, 5 equiv.). The mixture was heated at 85° C. for 16 hours, after which HPLC analysis indicated complete conversion to 6-(4-bromo-2-chlorophenylamino)-7-fluoro-3-methyl-3H-benzoimidazole-5-carboxylic acid. $^1$H NMR (400 MHz, DMSO-d$_6$) δ 3.92 (3H, s, CH$_3$), 6.50 (1H, apparent t, J 6.2-8.6, Ar—H), 7.31 (1H, d, J 8.8, Ar—H), 7.63 (1H, br s, Ar—H), 8.09 (1H, s, NH), 8.41 (1H, s, Ar—H). $^{19}$F NMR (376 MHz, DMSO-d$_6$) δ −133.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A process for preparing a compound of Formula Ia-2

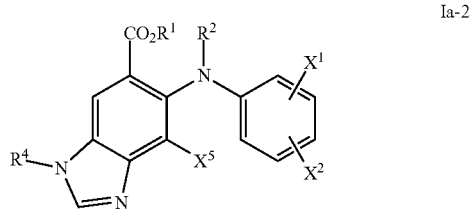

or a salt or solvate thereof, wherein:
R$^1$ is hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, trialkylsilyl or dialkylarylsilyl, wherein said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from halogen, hydroxyl, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl;

$R^2$ is hydrogen, $C_1$-$C_{10}$ alkyl, $C_2$-$C_{10}$ alkenyl, $C_2$-$C_{10}$ alkynyl, arylalkyl, trialkylsilyl, dialkylarylsilyl, —$COR^5$, —$C(O)OR^5$ or —$C(O)NR^5R^6$, wherein said alkyl, alkenyl, alkynyl, benzyl, allyl and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl;

$R^4$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, arylalkyl, heteroarylalkyl or heterocyclylalkyl, wherein said alkyl, alkenyl, alkynyl, cycloalkyl, cycloalkylalkyl, arylalkyl, heteroarylalkyl and heterocyclylalkyl portions are optionally substituted with one or more groups independently selected from halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^5R^6$ and —$OR^7$;

$X^1$ and $X^2$ are independently selected from hydrogen, F, Cl, Br, I, $OR^7$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl and $C_1$-$C_{10}$ thioalkyl, wherein said alkyl, alkenyl, alkynyl, cycloalkyl, cycloalkylalkyl and thioalkyl portions are optionally substituted with one or more groups independently selected from oxo, halogen, trifluoromethyl, difluoromethoxy and trifluoromethoxy;

$X^5$ is H, F, Cl, Br, I or $C_1$-$C_6$ alkyl;

$R^5$ and $R^6$ are independently hydrogen, trifluoromethyl, —$OR^7$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, or $R^5$ and $R^6$ together with the atom to which they are attached form a 4 to 10 membered heteroaryl or heterocyclic ring, wherein said heteroaryl and heterocyclic rings are optionally substituted with one or more groups independently selected from halogen, cyano, nitro, trifluoromethyl, difluoromethoxy, trifluoromethoxy, azido and $OR^7$; and $R^7$ is hydrogen, $C_1$-$C_{10}$ alkyl, $C_2$-$C_{10}$ alkenyl, aryl or arylalkyl, said method comprising:

reacting a compound of Formula Va or Vb

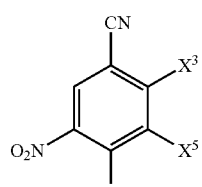

Va: A = $NR^3R^{3a}$
Vb: A = $N_3$ wherein $X^3$ is F, Cl, Br, I, or a sulfonate ester, $R^3$ is hydrogen, $C_1$-$C_{10}$ alkyl, $C_2$-$C_{10}$ alkenyl, $C_2$-$C_{10}$ alkynyl, benzyl, allyl, arylalkyl, trialkylsilyl, dialkylarylsilyl, —$COR^5$, —$C(O)OR^5$ or —$C(O)NR^5R^6$, wherein said alkyl, alkenyl, alkynyl, benzyl, allyl and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl, and $R^{3a}$ is hydrogen, substituted or unsubstituted benzyl, allyl or —$C(O)OR^6$, with a compound of Formula VI

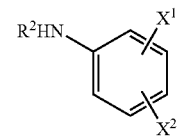

in the presence of a base to provide a compound of Formula VII-1a wherein A is —$NR^3R^{3a}$ or a compound of Formula VII-1b wherein A is $N_3$

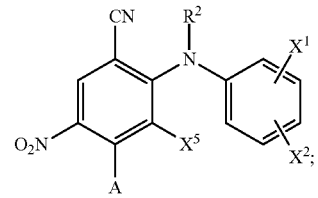

VII-1a: A = $NR^3R^{3a}$
VII-1b: A = $N_3$ reducing said compound of Formula VII-1a or VII-1b to provide a compound of Formula VIII-1

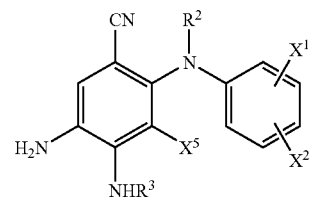

wherein when A of said compound of Formula VII-1a or VII-1b is $N_3$, NH-benzyl, NH-allyl, then $NHR^3$ of said compound of Formula VIII-1 is $NH_2$;

cyclizing said compound of Formula VIII-1 to provide a compound of Formula Ia-1

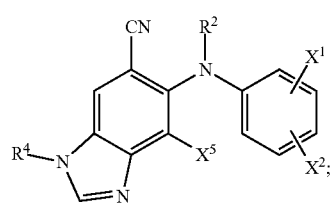

converting the nitrile group of said compound of Formula Ia-1 to $COOR^1$, to provide said compound of Formula Ia-2; and optionally preparing a salt or solvate of the compound of Formula Ia-2.

2. The process of claim 1, wherein said compound of Formula Va or Vb is prepared by the method comprising:

nitrating a compound of Formula IIa

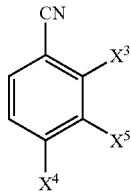

IIa wherein $X^3$ and $X^4$ are independently F, Cl, Br, I, or a sulfonate ester and $X^5$ is H, F, Cl, Br, I or $C_1$-$C_6$ alkyl to provide a compound of Formula IV

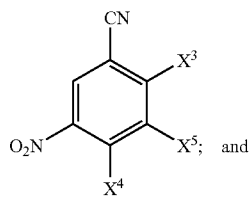

IV reacting said compound of Formula IV with (i) a reagent that contains or generates ammonia, (ii) a primary or secondary amine other than an aromatic amine or (iii) a reagent that delivers a group that can subsequently be converted into an amine, under conditions that allow selective displacement of $X^4$ of said compound of Formula IV, to provide said compound of Formula Va wherein A is $NR^3R^{3a}$; or reacting said compound of Formula IV with (iv) a metal azide under conditions that allow selective displacement of $X^4$ of said compound of Formula IV to provide said compound of Formula Vb wherein A is $N_3$.

3. The process of claim 1, wherein said compound of Formula Va or Vb is prepared by the method comprising:

nitrating a compound of Formula IIb

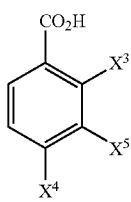

IIb wherein $X^3$ and $X^4$ are independently F, Cl, Br, I, or a sulfonate ester and $X^5$ is H, F, Cl, Br, I or $C_1$-$C_6$ alkyl to provide a compound of Formula III

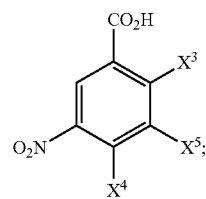

III converting the acid group of said compound of Formula III to a primary amide group to provide a compound of Formula IIId

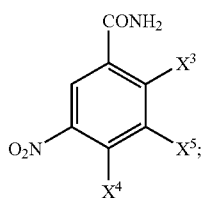

IIId converting said amide group of said compound of Formula IIId to a nitrile group to provide a compound of Formula IV

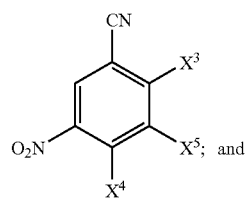

IV reacting said compound of Formula IV with (i) a reagent that contains or generates ammonia, (ii) a primary or secondary amine other than an aromatic amine or (iii) a reagent that delivers a group that can subsequently be converted into an amine, under conditions that allow selective displacement of $X^4$ of said compound of Formula IV, to provide said compound of Formula Va wherein A is $NR^3R^{3a}$; or reacting said compound of Formula IV with (iv) a metal azide under conditions that allow selective displacement of $X^4$ of said compound of Formula IV to provide said compound of Formula Vb wherein A is $N_3$.

4. The process of claim 1, wherein said compound of Formula Va or Vb is prepared by the method comprising:

nitrating a compound of Formula IIb

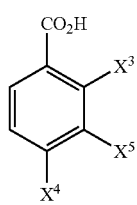

IIb wherein X³ and X⁴ are independently F, Cl, Br, I, or a sulfonate ester and X⁵ is H, F, Cl, Br, I or $C_1$-$C_6$ alkyl to provide a compound of Formula III

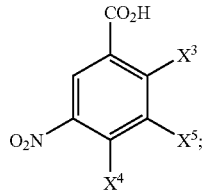

III reacting said compound of Formula III with (i) a reagent that contains or generates ammonia, (ii) a primary or secondary amine other than an aromatic amine or (iii) a reagent that delivers a group that can subsequently be converted into an amine, under conditions that allow selective displacement of X⁴ of said compound of Formula III, to provide a compound of Formula IIIa-1 wherein A is $NR^3R^{3a}$; or reacting said compound of Formula III with (iv) a metal azide under conditions that allow selective displacement of X⁴ of said compound of Formula III to provide a compound of Formula IIIa-2 wherein A is $N_3$

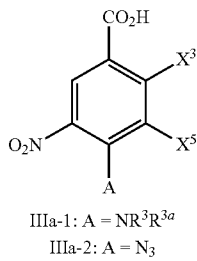

IIIa-1: A = $NR^3R^{3a}$
IIIa-2: A = $N_3$ wherein R³ is hydrogen, $C_1$-$C_{10}$ alkyl, $C_2$-$C_{10}$ alkenyl, $C_2$-$C_{10}$ alkynyl, benzyl, allyl, arylalkyl, trialkylsilyl, dialkylarylsilyl, —COR⁵, —C(O)OR⁵ or —C(O)NR⁵R⁶, wherein said alkyl, alkenyl, alkynyl, benzyl, allyl, and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl and $R^{3a}$ is hydrogen, substituted or unsubstituted benzyl, allyl or —C(O)OR⁶;

converting the carboxylic acid group of said compound of Formula IIIa-1 or IIIa-2 to a carboxylic acid ester to provide a compound of Formula IIIb-1 or IIIb-2

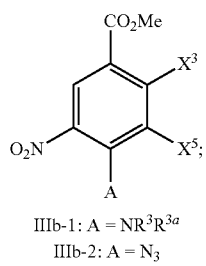

IIIb-1: A = $NR^3R^{3a}$
IIIb-2: A = $N_3$ converting the carboxylic acid ester group of said compound of Formula IIIb-1 or IIIb-2 to a primary amide group to provide a compound of Formula IIIc-1 or IIIc-2

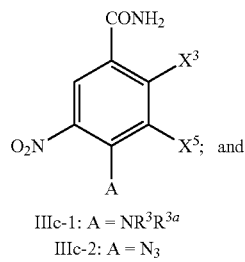

IIIc-1: A = $NR^3R^{3a}$
IIIc-2: A = $N_3$ dehydrating the primary amide group of said compound of Formula IIIc-1 or IIIc-2 to provide said compound of Formula Va or Vb.

5. The process of claim 2, wherein said reagent that contains or generates ammonia is $NH_3$ or $NH_4OH$.

6. The process of claim 5, wherein said compound of Formula IV is reacted with excess ammonium hydroxide in water at room temperature.

7. The process of claim 5, wherein said compound of Formula IV is reacted with aqueous ammonia at temperatures between 30 and 130° C. under 1-5 bar $NH_{3(g)}$.

8. The process of claim 2, wherein said primary or secondary amine is methylamine, benzylamine, dibenzylamine, allylamine, diallylamine or hexamethyldisilazane.

9. The process of claim 2, wherein said reagent that delivers a group that can subsequently be converted into an amine is selected from (a) a metal amide; (b) a protected ammonia or amide equivalent; (c) a nitrogen nucleophile having the Formula $MNR^3R^{3a}$ wherein M is a metal selected from Na, K, Li, Cs and Al; and (d) a metal silylamide.

10. The process of claim 9, wherein said metal amide is $NaNH_2$, $KNH_2$ or $LiNH_2$.

11. The process of claim 9, wherein said protected ammonia or amide equivalent is a hydroxylamine or a hydrazine.

12. The process of claim 9, wherein said metal silylamide is lithium (bis)(trimethylsilyl)amide, sodium (bis)(trimethylsilyl)amide or potassium (bis)(trimethylsilyl)amide.

13. The process of any claim 2, wherein said metal azide is $NaN_3$, $KN_3$ or $LiN_3$.

14. The process of claim 1, wherein said cyclization comprises reacting said compound of Formula VIII-1, wherein R³ is hydrogen, with (i) formic acid, optionally in the presence of a second acid or (ii) a formic acid derivative in the presence of an acid to provide said compound of Formula Ia-1 wherein R⁴ is hydrogen.

15. The process of claim 1, wherein said cyclization comprises reacting said compound of Formula VIII-1, wherein R³ is hydrogen, with two or more equivalents of formaldehyde or a formaldehyde derivative in the presence of an acid to provide said compound of Formula Ia-1 wherein R⁴ is methyl.

16. The process of claim 1, wherein said cyclization comprises:

(a) (i) reacting a compound of Formula VIII-1, wherein R³ is hydrogen, with an acylating agent to provide a compound of Formula IX-1

IX-1

[structure: benzene ring with CN, NR²-aryl(X¹,X²), X⁵, NHR³, and R⁴ᵃ-C(O)-NH- substituents]

wherein $R^{4a}$ is H, $C_1$-$C_{10}$ alkyl, $C_3$-$C_{10}$ cycloalkylalkyl, arylalkyl, heteroarylalkyl or heterocyclylalkyl, and (ii) reducing the amide group of said compound of Formula IX-1 to provide a compound of Formula X-1

X-1

[structure: benzene ring with CN, NR²-aryl(X¹,X²), X⁵, NHR³, and R⁴ᵃ-CH₂-NH- substituents]

(b) reacting said compound of Formula VIII-1, wherein $R^3$ is hydrogen, with an alkylating agent to provide said compound of Formula X-1; and (c) reacting said compound of Formula X-1 with (i) formic acid optionally in the presence of a second acid or (ii) a formic acid derivative in the presence of a second acid to provide said compound of Formula Ia-1 wherein $R^4$ is not hydrogen.

17. The process of claim 1, wherein said cyclization comprises:

(a) (i) reacting a compound of Formula VIII-1, wherein $R^3$ is not hydrogen, with an acylating agent to provide a compound of Formula IX-1

IX-1

[structure same as above IX-1]

wherein $R^{4a}$ is H, $C_1$-$C_{10}$ alkyl, $C_3$-$C_{10}$ cycloalkylalkyl, arylalkyl, heteroarylalkyl or heterocyclylalkyl, and (ii) reducing the amide group of said compound of Formula IX-1 to provide a compound of Formula X-1

X-1

[structure same as above X-1]

(b) reacting said compound of Formula VIII-1, wherein $R^3$ is not hydrogen, with an alkylating agent to provide said compound of Formula X-1;

(c) reacting said compound of Formula X-1 with (i) formic acid optionally in the presence of a second acid or (ii) a formic acid derivative in the presence of a second acid to provide said compound of Formula XI-1

XI-1

[structure: benzimidazolium cation fused benzene with CN, NR²-aryl(X¹,X²), X⁵, R⁴-N⁺, N-R³]

(d) removing the $R^3$ group to provide said compound of Formula Ia-1 wherein $R^4$ is not hydrogen.

18. The process of claim 14, wherein said formic acid derivative comprises an ester of formic acid.

19. The process of claim 18, wherein said formic acid ester is trimethylorthoformate, triethylorthoformate, or formamidine acetate.

20. The process of claim 15, wherein said formaldehyde derivative is a dialkoxymethane.

21. The process of claim 1, wherein the conversion of said nitrile group to $COOR^1$ group comprises treating said compound of Formula Ia-1 with water or an alcohol in the presence of an acid or base, with or without an organic cosolvent.

22. The process of claim 1, wherein said conversion of said nitrile group to $COOR^1$ comprises treating said compound of Formula Ia-1 with a nitrilase to provide said compound of Formula Ia-2 wherein $R^1$ is H.

23. A process for preparing a compound of Formula Ia-2

Ia-2

[structure: benzimidazole fused with benzene bearing CO₂R¹, NR²-aryl(X¹,X²), X⁵, R⁴-N, N]

or a salt or solvate thereof, wherein:

$R^1$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, trialkylsilyl or dialkylarylsilyl, wherein said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from halogen, hydroxyl, $C_1$-$C_4$ alkyl, $C_2$-$C_4$ alkenyl, $C_2$-$C_4$ alkynyl, $C_3$-$C_6$ cycloalkyl and $C_3$-$C_6$ heterocycloalkyl;

$R^2$ is hydrogen, $C_1$-$C_{10}$ alkyl, $C_2$-$C_{10}$ alkenyl, $C_2$-$C_{10}$ alkynyl, arylalkyl, trialkylsilyl, dialkylarylsilyl, —$COR^5$, —$C(O)OR^5$ or —$C(O)NR^5R^6$, wherein said alkyl, alkenyl, alkynyl, benzyl, allyl and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl;

$R^4$ is hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, arylalkyl, heteroarylalkyl or heterocyclylalkyl, wherein said alkyl, alkenyl, alkynyl, cycloalkyl, cycloalkylalkyl, arylalkyl, heteroarylalkyl, and heterocyclylalkyl portions are optionally substituted with one or more groups independently selected from halogen, hydroxyl, cyano, nitro, azido, $C_1$-$C_4$ alkyl, $C_2$-$C_4$ alkenyl, $C_2$-$C_4$ alkynyl, $C_3$-$C_6$ cycloalkyl, $C_3$-$C_6$ heterocycloalkyl, —$NR^5R^6$ and —$OR^7$;

$X^1$ and $X^2$ are independently selected from hydrogen, F, Cl, Br, I, $OR^7$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl and $C_1$-$C_{10}$ thioalkyl, wherein said alkyl, alkenyl, alkynyl, cycloalkyl, cycloalkylalkyl and thioalkyl portions are optionally substituted with one or more groups independently selected from oxo, halogen, trifluoromethyl, difluoromethoxy and trifluoromethoxy;

$X^5$ is H, F, Cl, Br, I or $C_1$-$C_6$ alkyl;

$R^5$ and $R^6$ are independently hydrogen, trifluoromethyl, —$OR^7$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, or $R^5$ and $R^6$ together with the atom to which they are attached form a 4 to 10 membered heteroaryl or heterocyclic ring, wherein said heteroaryl and heterocyclic rings are optionally substituted with one or more groups independently selected from halogen, cyano, nitro, trifluoromethyl, difluoromethoxy, trifluoromethoxy, azido and $OR^7$; and $R^7$ is hydrogen, $C_1$-$C_{10}$ alkyl, $C_2$-$C_{10}$ alkenyl, aryl or arylalkyl, said method comprising:

reacting a compound of Formula IV

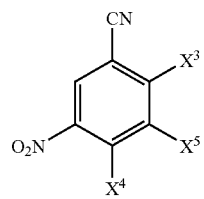

IV wherein $X^3$ and $X^4$ are independently F, Cl, Br, I or a sulfonate ester, with (i) a reagent that contains or generates ammonia, (ii) a primary or secondary amine other than an aromatic amine or (iii) a reagent that delivers a group that can subsequently be converted into an amine, under conditions that allow selective displacement of $X^4$ of said compound of Formula IV, to provide a compound of Formula Va wherein A is $NR^3R^{3a}$; or reacting said compound of Formula IV with (iv) a metal azide under conditions that allow selective displacement of $X^4$ of said compound of Formula IV to provide a compound of Formula Vb wherein A is $N_3$

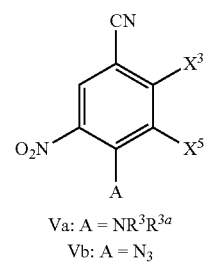

Va: A = $NR^3R^{3a}$
Vb: A = $N_3$ wherein $R^3$ is hydrogen, $C_1$-$C_{10}$ alkyl, $C_2$-$C_{10}$ alkenyl, $C_2$-$C_{10}$ alkynyl, benzyl, allyl, arylalkyl, trialkylsilyl, dialkylarylsilyl, —$COR^5$, —$C(O)OR^5$ or —$C(O)NR^5R^6$, wherein said alkyl, alkenyl, alkynyl, benzyl, allyl and arylalkyl portions are optionally substituted with one or more groups independently selected from halogen, hydroxyl, $C_1$-$C_4$ alkyl, $C_2$-$C_4$ alkenyl and $C_2$-$C_4$ alkynyl, and $R^{3a}$ is hydrogen, substituted or unsubstituted benzyl, allyl or —$C(O)OR^6$;

reacting said compound of Formula Va or Vb with a compound of the Formula VI

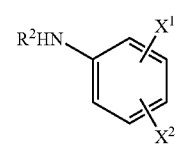

VI in the presence of a base to provide a compound having Formula VII-1a wherein A is —$NR^3R^{3a}$ or a compound of Formula VII-1b wherein A is $N_3$

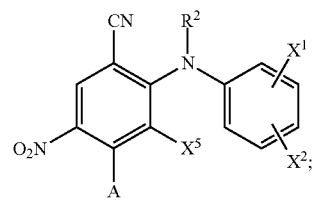

VII-1a: A = $NR^3R^{3a}$
VII-1b: A = $N_3$ reducing said compound of Formula VII-1a or VII-1b to provide a compound of Formula VIII-1

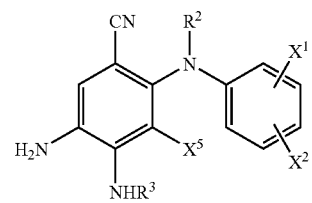

VIII-1 wherein when A of said compound of Formula VII-1a or VII-1b is $N_3$, NH-benzyl, NH-allyl, then $NHR^3$ of said compound of Formula VIII-1 is $NH_2$;

converting the nitrile group of said compound of Formula VIII-1 to $COOR^1$, to provide a compound of Formula VIII-2

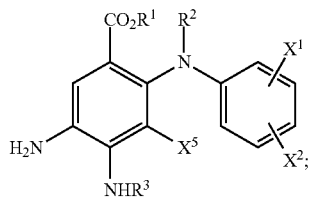

cyclizing said compound of Formula VIII-2 to provide said compound of Formula Ia-2; and optionally preparing a salt or solvate of the compound of Formula Ia-2.

24. A process for preparing a compound of Formula Ia-2

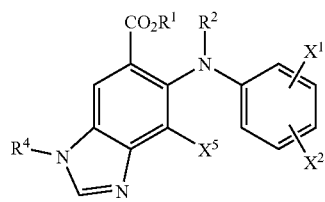

or a salt or solvate thereof, wherein:

R$^1$ is hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, trialkylsilyl or dialkylarylsilyl, wherein said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from halogen, hydroxyl, C$_1$-C$_4$ alkyl, C$_2$-C$_4$ alkenyl, C$_2$-C$_4$ alkynyl, C$_3$-C$_6$ cycloalkyl and C$_3$-C$_6$ heterocycloalkyl;

R$^2$ is hydrogen, C$_1$-C$_{10}$ alkyl, C$_2$-C$_{10}$ alkenyl, C$_2$-C$_{10}$ alkynyl, arylalkyl, trialkylsilyl, dialkylarylsilyl, —COR$^5$, —C(O)OR$^5$ or —C(O)NR$^5$R$^6$, wherein said alkyl, alkenyl, alkynyl, benzyl, allyl and arylalkyl portions are optionally substituted with one or more groups independently selected from halogen, hydroxyl, C$_1$-C$_4$ alkyl, C$_2$-C$_4$ alkenyl and C$_2$-C$_4$ alkynyl;

R$^4$ is hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, arylalkyl, heteroarylalkyl or heterocyclylalkyl, wherein said alkyl, alkenyl, alkynyl, cycloalkyl, cycloalkylalkyl, arylalkyl, heteroarylalkyl and heterocyclylalkyl portions are optionally substituted with one or more groups independently selected from halogen, hydroxyl, cyano, nitro, azido, C$_1$-C$_4$ alkyl, C$_2$-C$_4$ alkenyl, C$_2$-C$_4$ alkynyl, C$_3$-C$_6$ cycloalkyl, C$_3$-C$_6$ heterocycloalkyl, —NR$^5$R$^6$ and —OR$^7$;

X$^1$ and X$^2$ are independently selected from hydrogen, F, Cl, Br, I, OR$^7$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl and C$_1$-C$_{10}$ thioalkyl, wherein said alkyl, alkenyl, alkynyl, cycloalkyl, cycloalkylalkyl and thioalkyl portions are optionally substituted with one or more groups independently selected from oxo, halogen, trifluoromethyl, difluoromethoxy and trifluoromethoxy;

X$^5$ is H, F, Cl, Br, I or C$_1$-C$_6$ alkyl;

R$^5$ and R$^6$ are independently hydrogen, trifluoromethyl, —OR$^7$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl or heterocyclylalkyl, or R$^5$ and R$^6$ together with the atom to which they are attached form a 4 to 10 membered heteroaryl or heterocyclic ring, wherein said heteroaryl and heterocyclic rings are optionally substituted with one or more groups independently selected from halogen, cyano, nitro, trifluoromethyl, difluoromethoxy, trifluoromethoxy, azido and OR$^7$; and R$^7$ is hydrogen, C$_1$-C$_{10}$ alkyl, C$_2$-C$_{10}$ alkenyl, aryl or arylalkyl, said method comprising:

reacting a compound of Formula IV

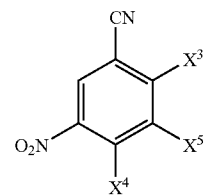

wherein X$^3$ and X$^4$ are independently F, Cl, Br, I or a sulfonate ester, with (i) a reagent that contains or generates ammonia, (ii) a primary or secondary amine other than an aromatic amine or (iii) a reagent that delivers a group that can subsequently be converted into an amine, under conditions that allow selective displacement of X$^4$ of said compound of Formula IV, to provide a compound of Formula Va wherein A is NR$^3$R$^{3a}$; or reacting said compound of Formula IV with (iv) a metal azide under conditions that allow selective displacement of X$^4$ of said compound of Formula IV to provide a compound of Formula Vb wherein A is N$_3$

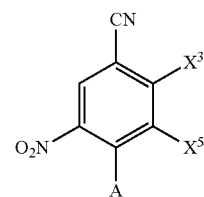

Va: A = NR$^3$R$^{3a}$
Vb: A = N$_3$ wherein R$^3$ is hydrogen, C$_1$-C$_{10}$ alkyl, C$_2$-C$_{10}$ alkenyl, C$_2$-C$_{10}$ alkynyl, benzyl, allyl, arylalkyl, trialkylsilyl, dialkylarylsilyl, —COR$^5$, —C(O)OR$^5$ or —C(O)NR$^5$R$^6$, wherein said alkyl, alkenyl, alkynyl, benzyl, allyl, and arylalkyl portions are optionally substituted with one or more groups independently selected from halogen, hydroxyl, C$_1$-C$_4$ alkyl, C$_2$-C$_4$ alkenyl and C$_2$-C$_4$ alkynyl, and R$^{3a}$ is hydrogen, substituted or unsubstituted benzyl, allyl or —C(O)OR$^6$;

reacting said compound of Formula Va or Vb with a compound of the Formula VI

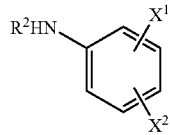

in the presence of a base to provide a compound having Formula VII-1a wherein A is —NR$^3$R$^{3a}$ or a compound of Formula VII-1b wherein A is N$_3$

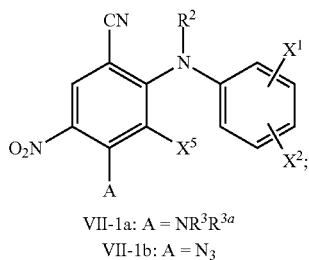

VII-1a: A = NR$^3$R$^{3a}$
VII-1b: A = N$_3$ converting the nitrile group of said compound of Formula VII-1a or VII-1b to COOR$^1$, to provide a compound of Formula VII-2a wherein A is NR$^3$R$^{3a}$ or VII-2b wherein A is N$_3$

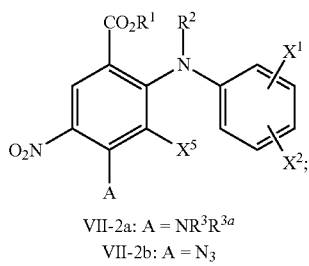

VII-2a: A = NR$^3$R$^{3a}$
VII-2b: A = N$_3$ reducing said compound of Formula VII-2a or VII-2b to provide a compound of Formula VIII-2

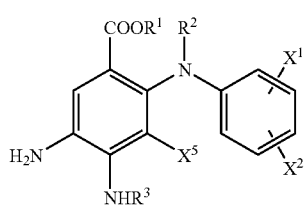

VIII-2 wherein when A of said compound of Formula VII-2a or VII-2b is N$_3$, NH-benzyl, NH-allyl, then NHR$^3$ of said compound of Formula VIII-2 is NH$_2$;

cyclizing said compound of Formula VIII-2 to provide said compound of Formula Ia-2; and optionally preparing a salt or solvate of the compound of Formula Ia-2.

25. A process for preparing a compound of Formula Ib-2

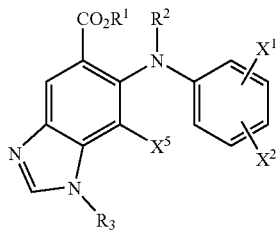

Ib-2 or a salt or solvate thereof, wherein:

R$^1$ is hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, trialkylsilyl or dialkylarylsilyl, wherein said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from halogen, hydroxyl, C$_1$-C$_4$ alkyl, C$_2$-C$_4$ alkenyl, C$_2$-C$_4$ alkynyl, C$_3$-C$_6$ cycloalkyl and C$_3$-C$_6$ heterocycloalkyl;

R$^2$ is hydrogen, C$_1$-C$_{10}$ alkyl, C$_2$-C$_{10}$ alkenyl, C$_2$-C$_{10}$ alkynyl, arylalkyl, trialkylsilyl, dialkylarylsilyl, —COR$^5$, —C(O)OR$^5$ or —C(O)NR$^5$R$^6$, wherein said alkyl, alkenyl, alkynyl, benzyl, allyl and arylalkyl portions are optionally substituted with one or more groups independently selected from halogen, hydroxyl, C$_1$-C$_4$ alkyl, C$_2$-C$_4$ alkenyl and C$_2$-C$_4$ alkynyl;

R$^3$ is C$_1$-C$_{10}$ alkyl, C$_2$-C$_{10}$ alkenyl, C$_2$-C$_{10}$ alkynyl, benzyl, allyl, arylalkyl, trialkylsilyl, dialkylarylsilyl, —COR$^5$, —C(O)OR$^5$ or —C(O)NR$^5$R$^6$, wherein said alkyl, alkenyl, alkynyl, benzyl, allyl and arylalkyl portions are optionally substituted with one or more groups independently selected from halogen, hydroxyl, C$_1$-C$_4$ alkyl, C$_2$-C$_4$ alkenyl and C$_2$-C$_4$ alkynyl;

X$^1$ and X$^2$ are independently selected from hydrogen, F, Cl, Br, I, OR$^7$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl and C$_1$-C$_{10}$ thioalkyl, wherein said alkyl, alkenyl, alkynyl, cycloalkyl, cycloalkylalkyl and thioalkyl portions are optionally substituted with one or more groups independently selected from oxo, halogen, trifluoromethyl, difluoromethoxy and trifluoromethoxy;

X$^5$ is H, F, Cl, Br, I or C$_1$-C$_6$ alkyl;

R$^5$ and R$^6$ are independently hydrogen, trifluoromethyl, —OR$^7$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl or heterocyclylalkyl, or R$^5$ and R$^6$ together with the atom to which they are attached form a 4 to 10 membered heteroaryl or heterocyclic ring, wherein said heteroaryl and heterocyclic rings are optionally substituted with one or more groups independently selected from halogen, cyano, nitro, trifluoromethyl, difluoromethoxy, trifluoromethoxy, azido and OR$^7$; and $R^7$ is hydrogen, $C_1$-$C_{10}$ alkyl, $C_2$-$C_{10}$ alkenyl, aryl or arylalkyl, said method comprising:

reacting a compound of Formula IV

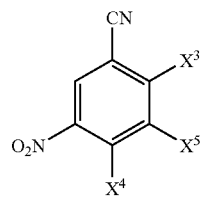

IV wherein $X^3$ and $X^4$ are independently F, Cl, Br, I, or a sulfonate ester, with (i) a reagent that contains or generates ammonia, (ii) a primary or secondary amine other than an aromatic amine or (iii) a reagent that delivers a group that can subsequently be converted into an amine, under conditions that allow selective displacement of $X^4$ of said compound of Formula IV, to provide a compound of Formula Va wherein A is $NR^3R^{3a}$; or reacting said compound of Formula IV with (iv) a metal azide under conditions that allow selective displacement of $X^4$ of said compound of Formula IV to provide a compound of Formula Vb wherein A is $N_3$

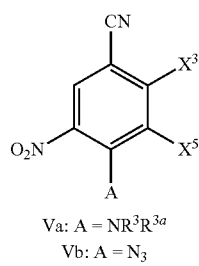

Va: A = $NR^3R^{3a}$
Vb: A = $N_3$ wherein $R^{3a}$ is hydrogen, substituted or unsubstituted benzyl, allyl or —C(O)$OR^6$;

reacting said compound of Formula Va or Vb with a compound of the Formula VI,

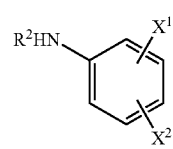

VI in the presence of a base to provide a compound having Formula VII-1a wherein A is —$NR^3R^{3a}$ or a compound of Formula VII-1b wherein A is $N_3$

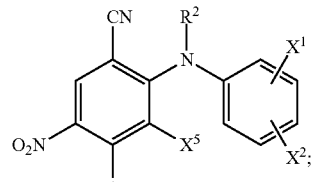

VII-1a: A = $NR^3R^{3a}$
VII-1b: A = $N_3$ reducing said compound of Formula VII-1a or VII-1b to provide a compound of Formula VIII-1

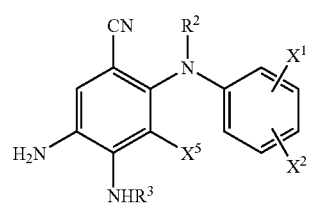

VIII-1 wherein when A of said compound of Formula VII-1a or VII-1b is $N_3$, NH-benzyl, NH-allyl, then $NHR^3$ of said compound of Formula VIII-1 is $NH_2$;

reacting said compound of Formula VIII-1 with (i) formic acid, optionally in the presence of a second acid, (ii) a formic acid derivative in the presence of an acid, or (iii) formaldehyde or a formaldehyde derivative in the presence of an acid to provide a compound of Formula Ib-1

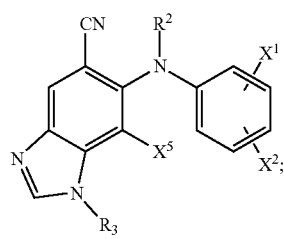

Ib-1 converting of the nitrile group of said compound of Formula Ib-1 to $COOR^1$, to provide said compound of Formula Ib-2; and optionally preparing a salt or solvate of the compound of Formula Ib-2.

26. The process of claim 3, wherein said reagent that contains or generates ammonia is $NH_3$ or $NH_4OH$.

27. The process of claim 26, wherein said compound of Formula IV is reacted with excess ammonium hydroxide in water at room temperature.

28. The process of claim 26, wherein said compound of Formula IV is reacted with aqueous ammonia at temperatures between 30 and 130° C. under 1-5 bar $NH_{3(g)}$.

29. The process of claim 4, wherein said reagent that contains or generates ammonia is $NH_3$ or $NH_4OH$.

30. The process of claim 3, wherein said primary or secondary amine is methylamine, benzylamine, dibenzylamine, allylamine, diallylamine or hexamethyldisilazane.

31. The process of claim 4, wherein said primary or secondary amine is methylamine, benzylamine, dibenzylamine, allylamine, diallylamine or hexamethyldisilazane.

32. The process of claim 3, wherein said metal azide is $NaN_3$, $KN_3$ or $LiN_3$.

33. The process of claim 4, wherein said metal azide is $NaN_3$, $KN_3$ or $LiN_3$.

34. The process of claim 16, wherein said formic acid derivative comprises an ester of formic acid.

35. The process of claim 34, wherein said formic acid ester is trimethylorthoformate, triethylorthoformate, or formamidine acetate.

36. The process of claim 17, wherein said formic acid derivative comprises an ester of formic acid.

37. The process of claim 36, wherein said formic acid ester is trimethylorthoformate, triethylorthoformate, or formamidine acetate.

38. The process of claim 3, wherein said reagent that delivers a group that can subsequently be converted into an amine is selected from (a) a metal amide; (b) a protected ammonia or amide equivalent; (c) a nitrogen nucleophile having the Formula $MNR^3R^{3a}$ wherein M is a metal selected from Na, K, Li, Cs and Al; and (d) a metal silylamide.

39. The process of claim 4, wherein said reagent that delivers a group that can subsequently be converted into an amine is selected from (a) a metal amide; (b) a protected ammonia or amide equivalent; (c) a nitrogen nucleophile having the Formula $MNR^3R^{3a}$ wherein M is a metal selected from Na, K, Li, Cs and Al; and (d) a metal silylamide.

* * * * *